United States Patent
Gono

(10) Patent No.: US 12,061,590 B2
(45) Date of Patent: Aug. 13, 2024

(54) INFORMATION PROCESSING SYSTEM AND PROCESSING METHOD

(71) Applicant: OLYMPUS CORPORATION, Tokyo (JP)

(72) Inventor: Kazuhiro Gono, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/989,160

(22) Filed: Nov. 17, 2022

(65) Prior Publication Data
US 2023/0153288 A1    May 18, 2023

Related U.S. Application Data

(60) Provisional application No. 63/294,509, filed on Dec. 29, 2021, provisional application No. 63/280,716, filed on Nov. 18, 2021.

(51) Int. Cl.
G06F 16/23    (2019.01)

(52) U.S. Cl.
CPC .................. G06F 16/23 (2019.01)

(58) Field of Classification Search
CPC ..................................... G06F 16/23
See application file for complete search history.

(56) References Cited

U.S. PATENT DOCUMENTS

| | | | |
|---|---|---|---|
| 7,953,612 B1 * | 5/2011 | Palmese | G16H 20/40 128/923 |
| 2004/0015329 A1 * | 1/2004 | Shayegan | G09B 23/28 702/179 |

| | | |
|---|---|---|
| 2007/0185377 A1 | 8/2007 | Murakami et al. |
| 2008/0214890 A1 | 9/2008 | Motai et al. |

(Continued)

FOREIGN PATENT DOCUMENTS

| | | |
|---|---|---|
| JP | H11-019027 A | 1/1999 |
| JP | 2003-038419 A | 2/2003 |

(Continued)

OTHER PUBLICATIONS

Yi et al. ("Quantitative Analysis of Colonoscopy Skills Using the KAIST-Ewha Colonoscopy Simulator II"; Frontier in the Convergence of Bioscience and Information Technologies 2007) (Year: 2007).*

(Continued)

*Primary Examiner* — Anhtai V Tran
*Assistant Examiner* — Ken Hoang
(74) *Attorney, Agent, or Firm* — Scully, Scott, Murphy & Presser, P.C.

(57) ABSTRACT

An information processing system comprises a processor including hardware. The processor is configured to acquire an evaluation parameter of a procedure performed by a doctor, calculate one or more evaluation items based on the evaluation parameter acquired, evaluate a first skill of the procedure based on the one or more evaluation items calculated, reference a training course based on the one or more evaluation items calculated and the first skill evaluated, and a database storing each of the one or more evaluation items in correspondence with training courses based on weighting coefficients, and perform processing of notifying a proposal of the training course referenced.

20 Claims, 18 Drawing Sheets

(56) References Cited

U.S. PATENT DOCUMENTS

| | | |
|---|---|---|
| 2008/0249356 A1 | 10/2008 | Motai et al. |
| 2008/0249358 A1 | 10/2008 | Motai et al. |
| 2010/0041949 A1 | 2/2010 | Tolkowsky |
| 2010/0056910 A1 | 3/2010 | Yanuma |
| 2014/0212849 A1 | 7/2014 | Naiwala et al. |
| 2015/0164608 A1* | 6/2015 | Bartenstein ............ A61B 5/06 606/130 |
| 2015/0265807 A1 | 9/2015 | Park et al. |
| 2016/0206228 A1* | 7/2016 | Angulo ................ A61B 5/061 |
| 2016/0338716 A1* | 11/2016 | Aslinia ................ A61B 17/10 |
| 2017/0086929 A1 | 3/2017 | Moll et al. |
| 2018/0040126 A1 | 2/2018 | Bayer |
| 2019/0029757 A1* | 1/2019 | Roh ...................... G16H 20/40 |
| 2019/0340956 A1* | 11/2019 | Lindkvist .............. G09B 23/30 |
| 2020/0178773 A1 | 6/2020 | Miller |
| 2021/0196398 A1 | 7/2021 | Ye et al. |
| 2022/0192466 A1 | 6/2022 | Nishimura |
| 2023/0148847 A1 | 5/2023 | Gono et al. |
| 2023/0148848 A1 | 5/2023 | Gono et al. |
| 2023/0148849 A1 | 5/2023 | Inoue et al. |
| 2023/0149043 A1 | 5/2023 | Gono et al. |

FOREIGN PATENT DOCUMENTS

| | | |
|---|---|---|
| JP | 2005-334474 A | 12/2005 |
| JP | 2008-253780 A | 10/2008 |
| JP | 2011-240152 A | 12/2011 |
| JP | 2012-213436 A | 11/2012 |
| JP | 2013-069251 A | 4/2013 |
| JP | 2019-197436 A | 11/2019 |
| WO | 2021/049475 A1 | 3/2021 |

OTHER PUBLICATIONS

Japanese Office Action dated Oct. 3, 2023 received in 2022-171250.
Extended European Search Report dated Apr. 5, 2023 received in 22207769.5.
Japanese Office Action dated Mar. 5, 2024 received in 2022-171250.

* cited by examiner

FIG.4
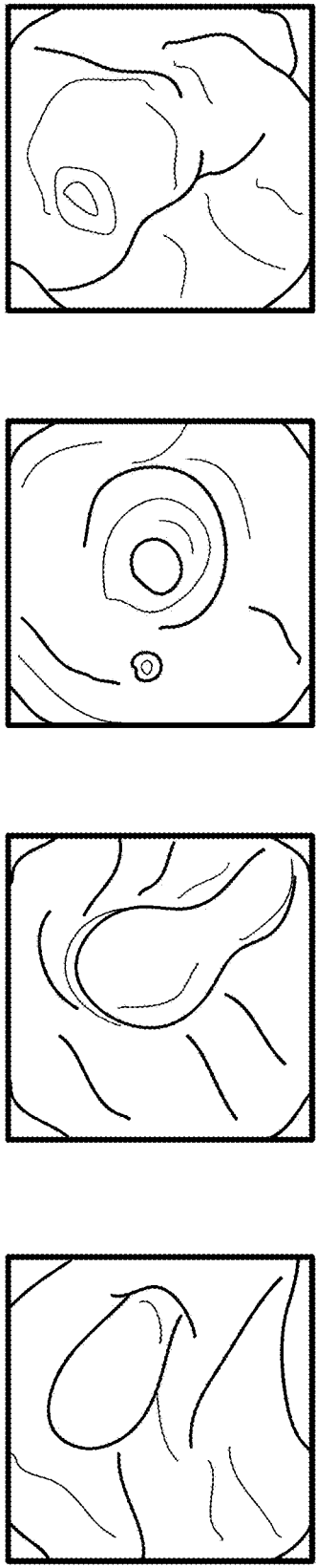
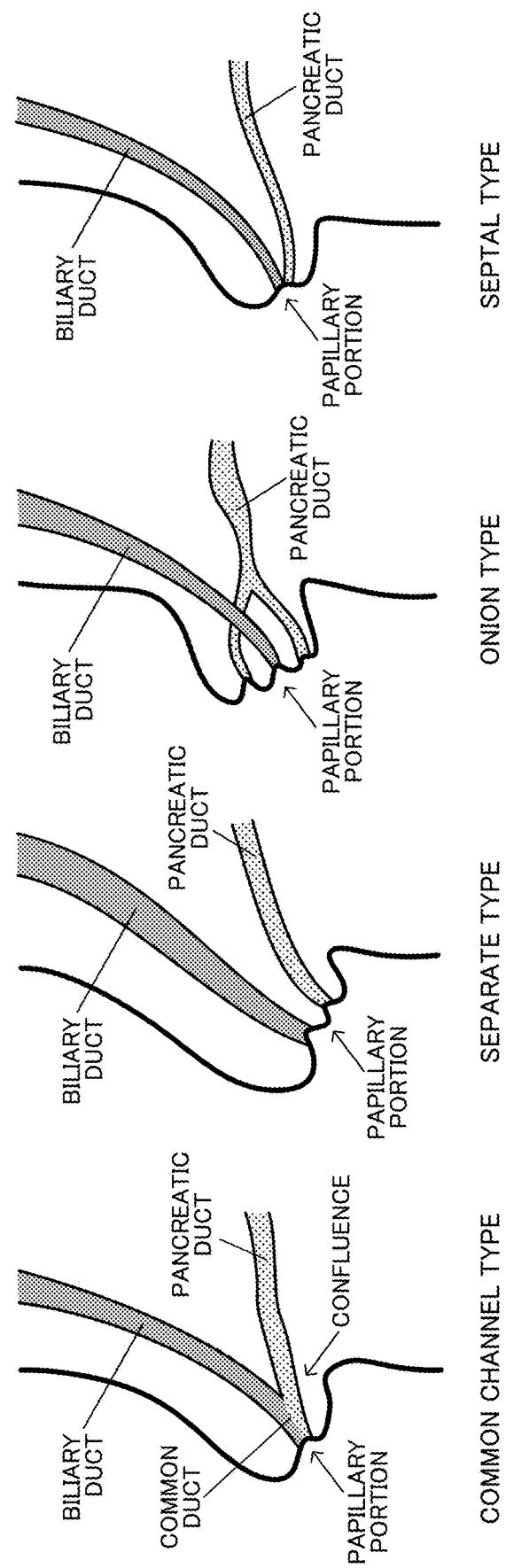

FIG.5
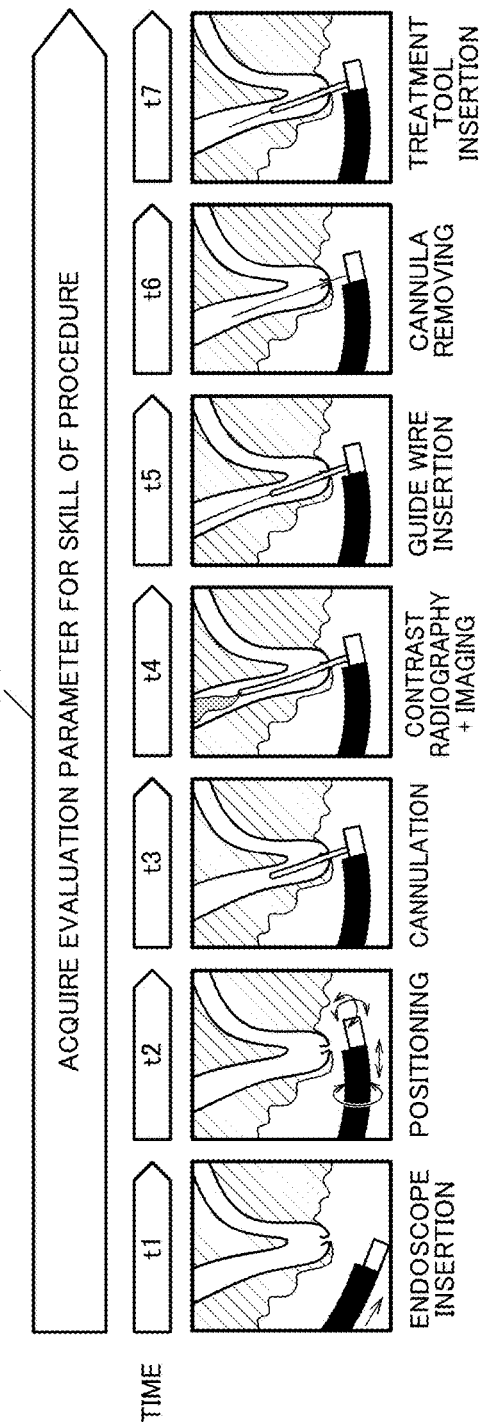
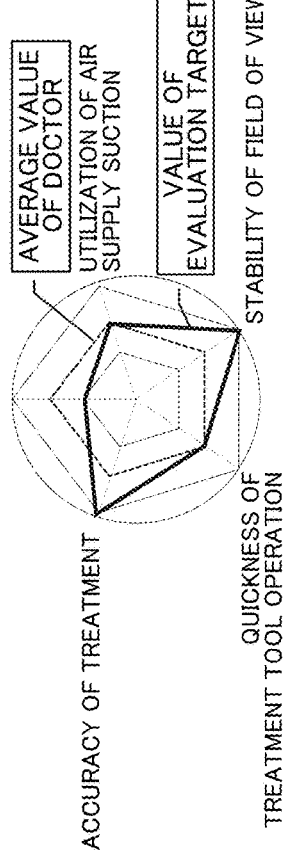

FIG.15

BEFORE TAKING THE COURSE

| TAKEN TRAINING COURSE | TRA |
|---|---|
| DATE OF TAKING COURSE | YEAR MONTH DAY |

| EVALUATION ITEM | EVALUATION RESULT |
|---|---|
| ENDOSCOPE INSERTION | EA1 |
| QUICKNESS OF TREATMENT TOOL OPERATION | EA2 |
| STABILITY OF FIELD OF VIEW | EA3 |
| UTILIZATION OF AIR SUPPLY SUCTION | EA4 |
| ACCURACY OF TREATMENT | EA5 |

AFTER TAKING THE COURSE

| EVALUATION ITEM | EVALUATION RESULT |
|---|---|
| ENDOSCOPE INSERTION | EB1 |
| QUICKNESS OF TREATMENT TOOL OPERATION | EB2 |
| STABILITY OF FIELD OF VIEW | EB3 |
| UTILIZATION OF AIR SUPPLY SUCTION | EB4 |
| STABILITY OF TREATMENT | EB5 |

INFORMATION PROCESSING SYSTEM AND PROCESSING METHOD

CROSS-REFERENCE TO RELATED APPLICATIONS

This application claims the benefit of U.S. Provisional Application No. 63/294,509, filed on Dec. 29, 2021, and U.S. Provisional Application No. 63/280,716, filed on Nov. 18, 2021. The entire content of U.S. Provisional Application No. 63/294,509 and U.S. Provisional Application No. 63/280,716 are incorporated herein by this reference.

DESCRIPTION OF RELATED ART

In procedures performed using an endoscope, a doctor may be required to perform appropriate operations in an unfavorable field of view of the endoscope under an unstable environment where his/her posture is not fixed. For this reason, there is a problem that procedures performed using an endoscope have a high degree of difficulty. For example, Japanese Patent Application Laid-Open No. 2019-197436 discloses a method of evaluating a doctor's skill level based on a ratio of insertion time required for inserting an endoscope to removal time required for pulling out the endoscope. Further, Japanese Patent Application Laid-Open No. 2013-69251 discloses a method of determining a driving skill of a car, and notifying driving advice.

SUMMARY

In accordance with one of some aspect, there is provided an information processing system comprising a processor including hardware. The processor is configured to acquire an evaluation parameter of a procedure performed by a doctor, calculate one or more evaluation items based on the evaluation parameter acquired, evaluate a first skill of the procedure based on the one of more evaluation items calculated, reference a training course based on the one or more evaluation items calculated and the first skill evaluated, and a database storing each of the one of more evaluation items in correspondence with training courses based on weighting coefficients, and perform processing of notifying a proposal of the training course referenced.

In accordance with one of some aspect, there is provided a processing method, comprising acquiring an evaluation parameter of a procedure performed by a doctor, calculating one or more evaluation items based on the evaluation parameter acquired, evaluating a first skill of the procedure based on the one or more evaluation items calculated, referencing a training course based on the one or more evaluation items calculated and the first skill evaluated, and a database storing each of the one or more evaluation items in correspondence with training courses based on weighting coefficients, and performing processing of notifying a proposal of the training course referenced.

BRIEF DESCRIPTION OF THE DRAWINGS

FIG. 4 shows classification types of a biliary duct and a pancreatic duct corresponding to an endoscope image of the papillary portion.

FIG. 5 is an explanatory diagram of a method according to the present embodiment.

FIG. 15 shows a specific example of the notification.

DETAILED DESCRIPTION

Figure 1:
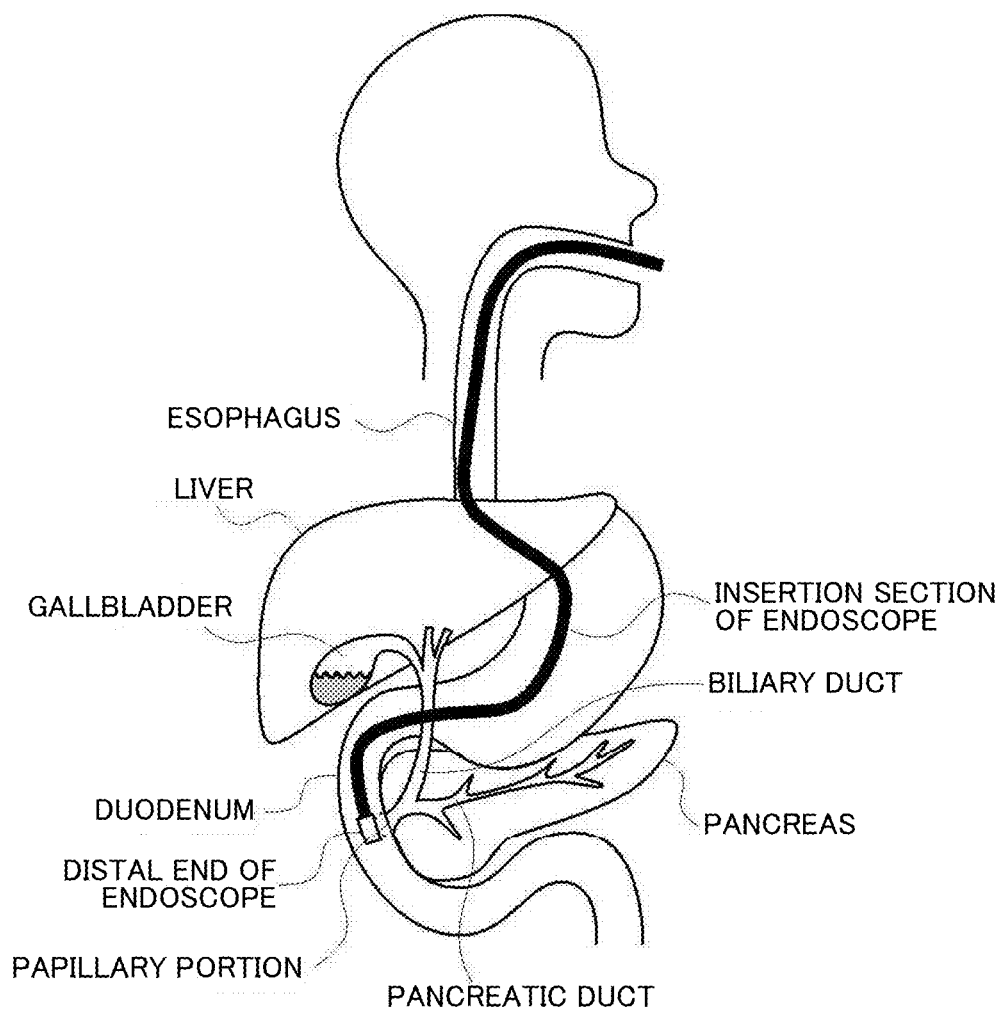
FIG. 1 shows organs and tissues involved in the ERCP procedure.

The following disclosure provides many different embodiments, or examples, for implementing different features of the provided subject matter. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

Procedure Using an Endoscope

There are various procedures performed using an endoscope, such as endoscopic retrograde cholangiopancreatography (ERCP), endoscopic mucosal resection (EMR), endoscopic submucosal dissection (ESD), endoscopic sphincterotomy (EST), endoscopic papillary balloon dilation (EPBD), endoscopic retrograde biliary drainage (ERBD) or transurethral ureterolithotripsy (TUL). Although a method according to the present embodiment can be applied to various procedures using such an endoscope, the contents of an ERCP procedure will be described before the method according to the present embodiment is described.

FIG. 1 shows organs and tissues involved in the ERCP procedure. The organs include a multiple types of tissues, forming a unique structure with a specific function. In FIG. 1, the liver, gallbladder, pancreas, esophagus, stomach, and duodenum are shown as organs. Tissues are formed by related cells combined, and examples include blood vessels, muscles, skin, and the like. In FIG. 1, a biliary duct and a pancreatic duct are shown as tissues.

The biliary duct is the target of the ERCP procedure. The biliary duct is a pipeline for allowing the bile produced in the liver to flow into the duodenum. When approaching the biliary duct using an endoscope, a treatment tool inserted into the channel of the endoscope is inserted to the biliary duct from the papillary portion of the duodenum while holding the endoscope at the position of the duodenum. Hereinafter, the papillary portion of the duodenum is simply referred to as a papillary portion. The papillary portion is a region including an opening of the luminal tissue with respect to the duodenum. Not only the opening but also the structure around the opening is referred to as a papillary portion. The opening of the luminal tissue is the opening of a common duct with respect to the duodenum. The common duct is formed as the confluence of the biliary duct and pancreatic duct. However, as described later, the papillary portion largely varies between individuals. For example, in some cases, the biliary duct opens directly to the duodenum without being merged with the pancreatic duct. In this case, the opening of the luminal tissue is the opening of the biliary duct.

Figure 2:
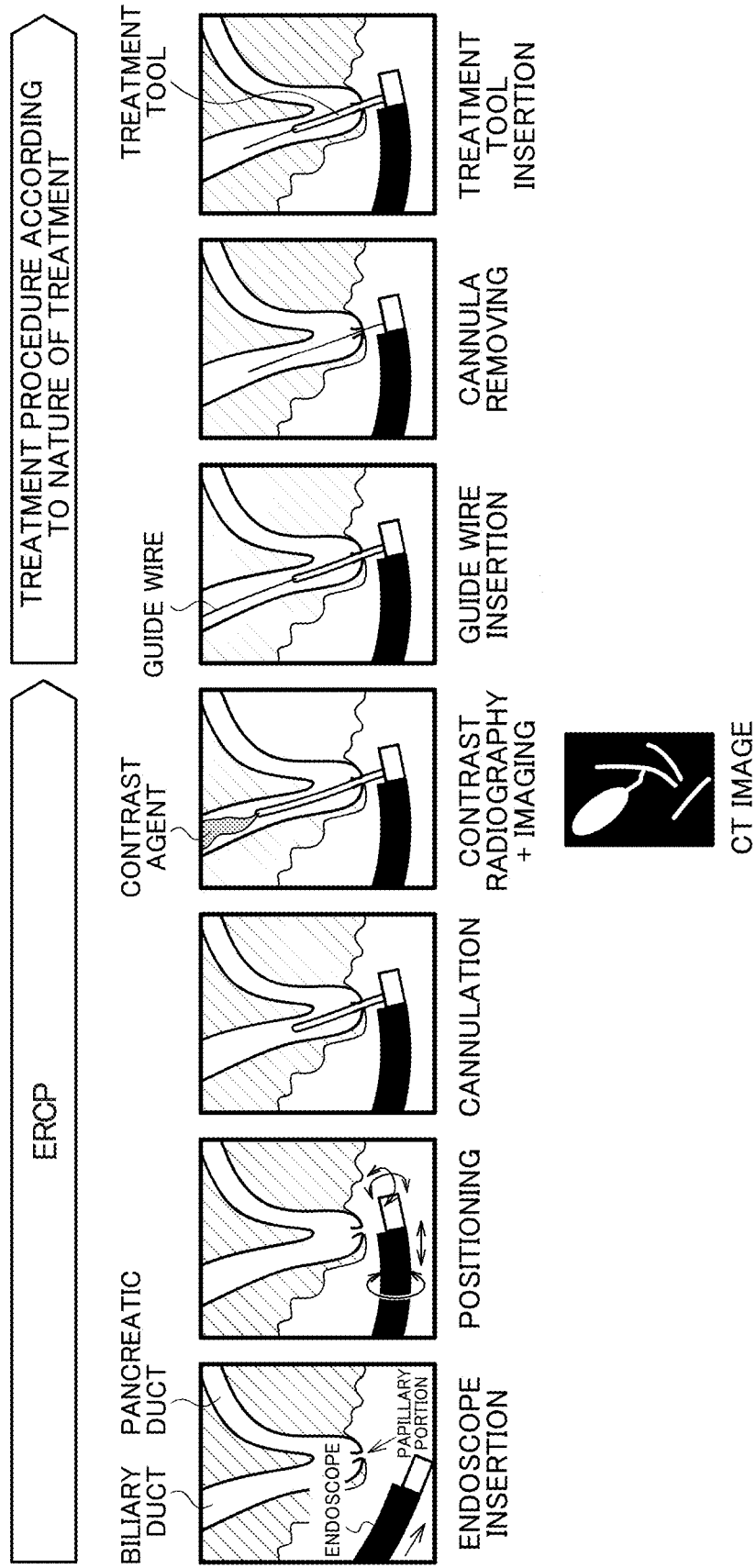
FIG. 2 shows a flow of the ERCP procedure.

FIG. 2 shows a flow of the ERCP procedure. In ERCP, a side-viewing type endoscope in which a camera, an illumination lens, and an opening of a treatment tool channel are provided on a side surface of a distal end section of the endoscope is used. The camera is also referred to as an imaging device.

In an endoscope insertion step, the insertion section of the endoscope is inserted from the mouth to the duodenum through the esophagus and stomach. At this time, the insertion section is inserted until the papillary portion becomes roughly visible in the field of view of the endoscope. Next, in a positioning step, the position of the endoscope is adjusted relative to the papillary portion. Specifically, the position of the distal end section of the endoscope is adjusted so that the papillary portion is within the imaging range of the camera of the endoscope. Alternatively, the position of the distal end section of the endoscope is adjusted so that the camera of the endoscope is facing directly front of the papillary portion and the papillary portion appears in the center of the field of view. The positioning step includes an alignment of the camera with respect to the target procedure area, an alignment of the treatment tool with respect to the target procedure area, an alignment of air and fluid supply and suction to the target procedure area, as well as an alignment of the camera or the treatment tool with respect to the duodenal papillary area.

Then, in a cannulation step, a cannula is inserted from the papillary portion into the biliary duct. Specifically, the cannula is inserted into the treatment tool channel of the endoscope so that the cannula protrudes from the channel opening of the distal end section of the endoscope. The distal end of the cannula is inserted into the common duct from the opening of the common duct, and the cannula is further inserted through the confluence of the biliary duct and the pancreatic duct toward the direction of the biliary duct. Cannulation refers to insertion of a cannula into a body. A cannula is a medical tube that is inserted into a body for medical purposes.

Next, in a contrast radiography and imaging step, a contrast agent is injected into the cannula and poured into the biliary duct through the distal end of the cannula. By performing X-ray or computerized tomography (CT) imaging in this state, an X-ray image or a CT image showing the biliary duct, gallbladder, and pancreatic duct can be acquired.

After the procedure, various treatments are performed according to the results of diagnosis based on the X-ray image or CT image. An example of the treatment is described below.

In a guide wire insertion step, a guide wire is inserted into a cannula so that the guide wire is protruded from the distal end of the cannula, and the guide wire is inserted into the biliary duct. In a cannula removing step, the cannula is removed while leaving the guide wire inside the biliary duct. As a result, only the guide wire protrudes from the distal end section of the endoscope, indwelling in the biliary duct. Next, in a treatment tool insertion step, the treatment tool is inserted into the biliary duct along the guide wire. An example of a treatment tool is a basket or stent. The basket is used with a catheter. While allowing the guide wire to pass through the catheter, the catheter is inserted into the biliary duct along the guide wire. A basket made of a plurality of metal wires is inserted into the biliary duct from the distal end of the catheter, an object to be removed, such as a gallstone, is placed in the basket and held, and the object to be removed is taken out from the biliary duct by removing the basket and catheter in this state from the biliary duct. A stent is also used in a similar manner with a catheter and inserted into the biliary duct from the distal end of the catheter. The narrow portion of the biliary duct can be widened by inserting a stent; further, by keeping the stent therein, the narrow portion is held in a widened state by the indwelling stent.

Figure 3:
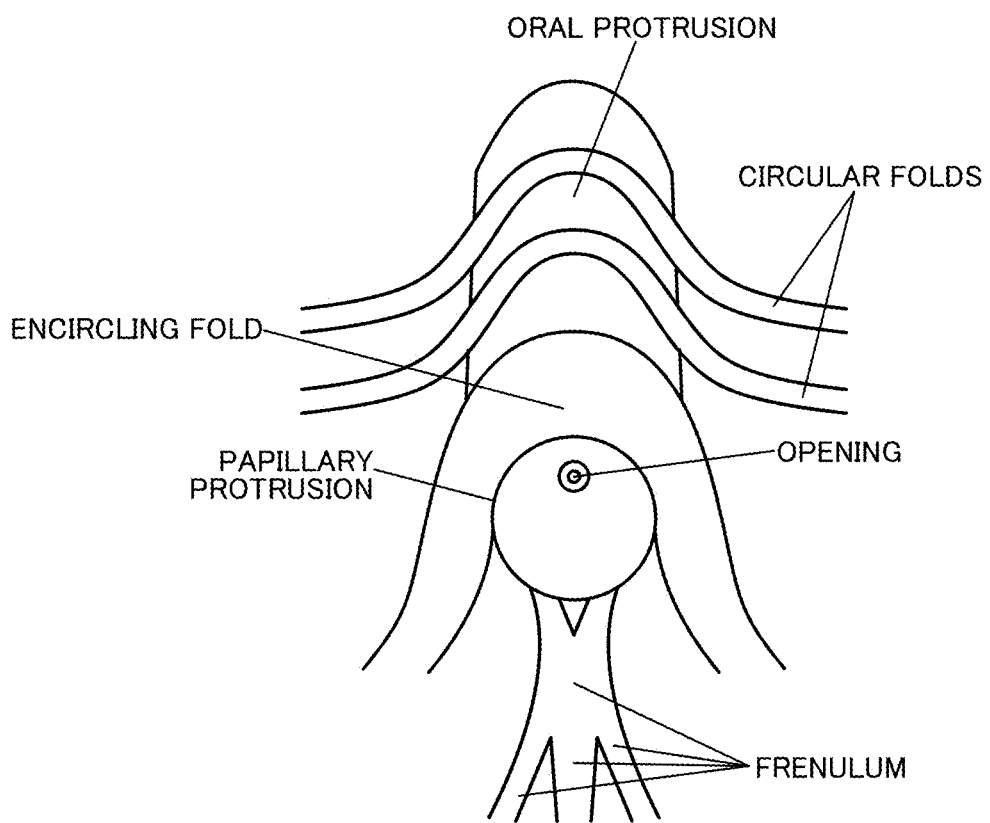
FIG. 3 shows a schematic diagram of the form of papillary portion viewed directly from the front.

Although the ERCP procedure is performed as described above, there is a problem that the ERCP procedure is a difficult procedure for an inexperienced doctor. For example, FIG. 3 is a diagram schematically showing the form of the papillary portion as viewed directly from the front thereof. As shown in FIG. 3, there is a unique structure around an opening of the papillary portion. Specifically, structures called frenula, papillary protrusions, encircling folds, circular folds, and oral protrusions exist around the opening, which is the main papillary portion. And as shown in FIG. 3, the opening of the papillary portion is often in a closed state. In some cases, the opening is tightly closed, and thus there is a problem that the cannula cannot be inserted smoothly.

In addition, there are individual differences in shapes of the opening and its surroundings in the papillary portion. For example, FIG. 4 shows examples of classification patterns of the papillary portion and endoscope images observed in each classification pattern. Examples of the classification pattern depending on the routes of the biliary duct and the pancreatic duct include for example, as shown in FIG. 4, a common duct type, a separated type, an onion type, a septal type and the like. Further, examples of the classification pattern depending on the opening of the papillary portion include another opening type, an onion type, a nodule type, a villous type, a flat type, and a vertically long type. In the cannulation step, only an endoscope image of the papillary portion from the outside can be observed from the field of view of the operator, and there is a problem that the direction of the biliary duct or pancreatic duct cannot be predicted from thitransmitoscope image. That is, since there are individual differences in the routes of the biliary duct and the pancreatic duct as shown in FIG. 4, it is difficult to predict the routes.

ERCP, which is a procedure using an endoscope in this way, is a difficult procedure for doctors. In addition to ERCP, there are various procedures using endoscopes, such as EMR, ESD, EST, EPBD, ERBD, TUL, and the like, and these procedures are also difficult for doctors and require high skills.

Notification of Training Courses Based on Skill Evaluation

As described above, there is a problem that the procedure performed using an endoscope is difficult for doctors with little experience. Therefore, in the present embodiment, a method of acquiring an evaluation parameter of a procedure performed by a doctor using an endoscope, evaluating the skill of the procedure performed by the doctor based on the evaluation parameter, and notifying a proposal of a training course for an endoscope skill based on a result of evaluating the skill, is adopted. FIG. 5 is a diagram illustrating such a method according to the present embodiment. In the following, although ERCP will be mainly described as an example of a procedure performed using an endoscope, as a procedure to which the method according to the present embodiment is applied, various procedures other than ERCP can be assumed as described above. Additionally, although ERCP is exactly up to the step of contrast radiography (and imaging) in FIG. 2, subsequent procedures including steps such as guide wire insertion, cannula removing, and treatment tool insertion will be referred to as ERCP for convenience of explanation.

First, as shown in step S11 in FIG. 5, an evaluation parameter for evaluating the skill of a procedure performed by a doctor using an endoscope is acquired. In an example of FIG. 5, each time t1, t2, t3, t4, t5, t6, and t7 required by the doctor for each step of endoscope insertion, positioning, cannulation, contrast radiography (and imaging), guide wire insertion, cannula removing, and treatment tool insertion is acquired as an evaluation parameter (evaluation parameter value). Then, in step S12, the skill of the doctor's procedure is evaluated for each evaluation item of a plurality of evaluation items based on the evaluation parameters acquired in step S11. In the example of FIG. 5, as a plurality of evaluation items, endoscope insertion, accuracy of treatment, quickness of treatment tool operation, stability of field of view, and utilization of air supply suction are prepared, and the skill of the doctor is evaluated based on the evaluation parameters for each of these evaluation items. For example, in FIG. 5, the doctor being an evaluation target is evaluated as having a high skill in the evaluation item for the accuracy of treatment and the stability of field of view, and is evaluated as having a low skill in the evaluation item for the endoscope insertion. Additionally, in FIG. 5, an average value of the doctor is also shown, and it is evaluated that the doctor's skill is average in terms of the evaluation items for the quickness of treatment tool operation and the utilization of air supply suction.

Then, in step S13, notification of a proposal of a training course for an endoscope skill is performed based on a result of evaluating the skill including a result of evaluating each evaluation item. For example, since the doctor being an evaluation target has a low evaluation for an endoscope insertion skill, he/she has been notified of a proposal to take an endoscope insertion course, which is a training course to improve his/her endoscope insertion skill. In this notification, the doctor would be notified of a training course, date and time and place where the course will be held, an application form, and the like. The training course proposed is associated with a lowest evaluation item that is evaluated low among the evaluation item in plurality. The processor 30 is configured to identify the lowest evaluation item among the one or more of the evaluation item, and determine the proposal of the training course based on lowest evaluation item.

Figure 6:
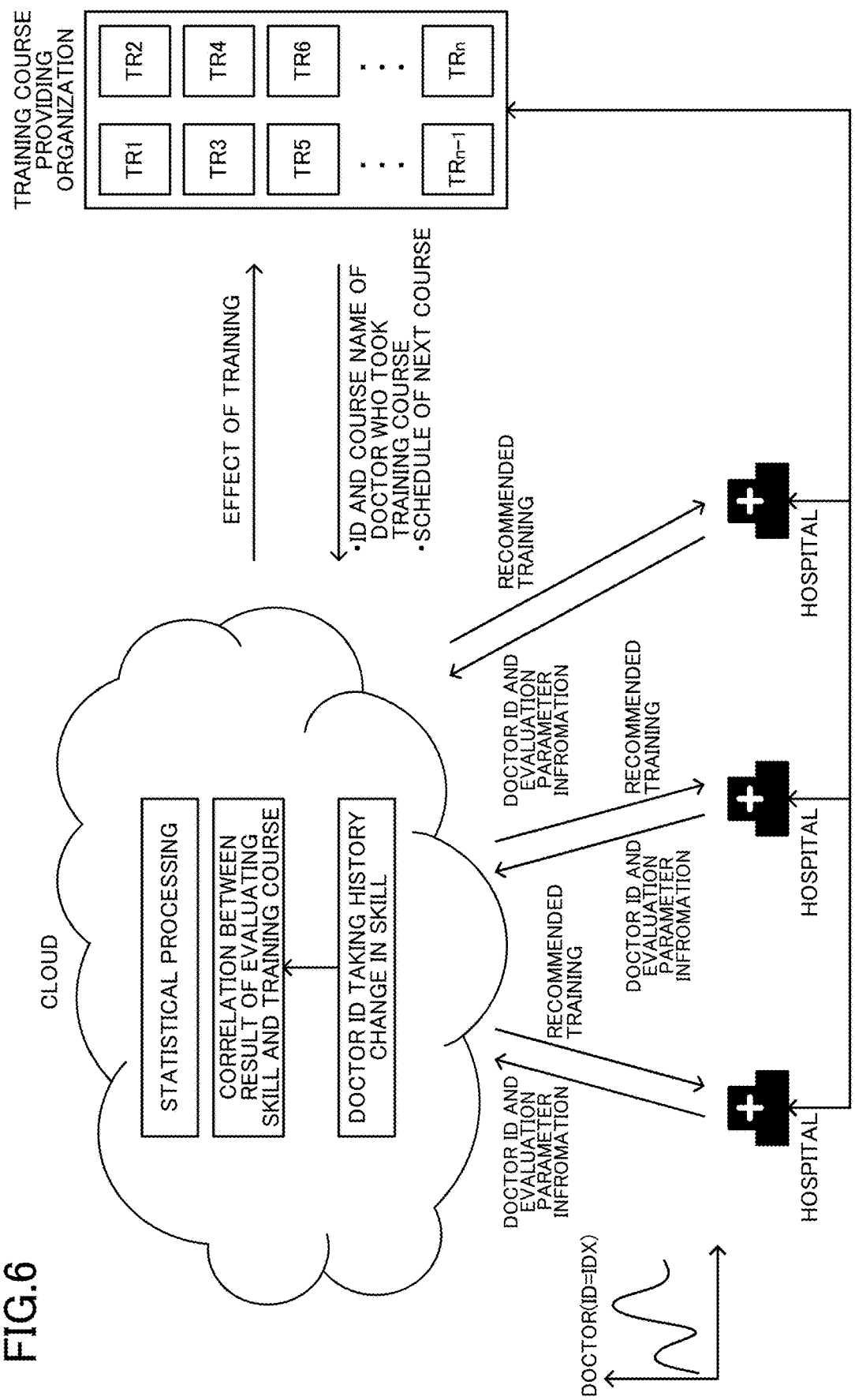
FIG. 6 shows an overall image of a system that achieves the method according to the present embodiment.

FIG. 6 shows an overall image of a system that achieves the method according to the present embodiment. At each hospital, doctors use endoscopes to perform treatments and examinations according to predetermined procedures. Then, the information of the evaluation parameters for evaluating the skill of the doctor's procedure at that time is transmitted (uploaded) to a cloud server. Specifically, information on evaluation parameters is transmitted in association with the ID of the doctor who performed the procedure. For example, the server is achieved by an information processing system 20 according to the present embodiment shown in FIG. 7, which will be described later. The information on evaluation parameters is information for specifying the value of the evaluation parameter. Referring to FIG. 5 as an example, the information on evaluation parameters is information for specifying the time required for each step of the procedures, and may be the time itself or the information by which the cloud server (information processing system) can specify the time of each step. For example, when an endoscope in which the endoscopic operation is electrically driven is used as described later, the information on evaluation parameters may be operation data input by the doctor using an operation device (operation section) of the endoscope. As will be described later with reference to FIG. 11, as the evaluation parameters, not only the evaluation parameter for the time required for each step of the procedures but also various parameters can be assumed.

Information such as the doctor's taking history and changes in skills is accumulated and stored in a database of the cloud server in association with the doctor's ID. Then, in the cloud server, the information accumulated in the database is used as big data, and a correlation between a result of evaluating the skill and a training course is specified. For example, a correlation is specified as to which training course is effective for a doctor to improve the evaluation of the skill of the procedure corresponding to the evaluation item. As a result, doctors at each hospital are notified of recommended training courses based on the result of evaluating the skill. In addition, statistical processing of the result of evaluating the skill is also performed on the cloud server. For example, as the statistical processing, the cloud server performs processing of calculation for ranking the result of evaluating the skill, acquires standard values such as the average value of skill evaluation, and performs processing of comparing the results of evaluating the skill before and after taking the training course.

Various training courses TR1 to TRn can be taken at a training course providing organization. The doctors at each hospital can then take training courses proposed by the cloud server at the training course providing organization. The effect of training by the training course is fed back from the cloud server to the training course providing organization. For example, the cloud server performs processing of comparing the results of evaluating the skill of the doctor before and after taking the training course, and feeds back a comparison result to the training course providing organization as the effect of training. On the other hand, the training course providing organization transmits the ID and course name of the doctor who took the training course, the schedule of a next training course, and the like to the cloud server.

Figure 7:
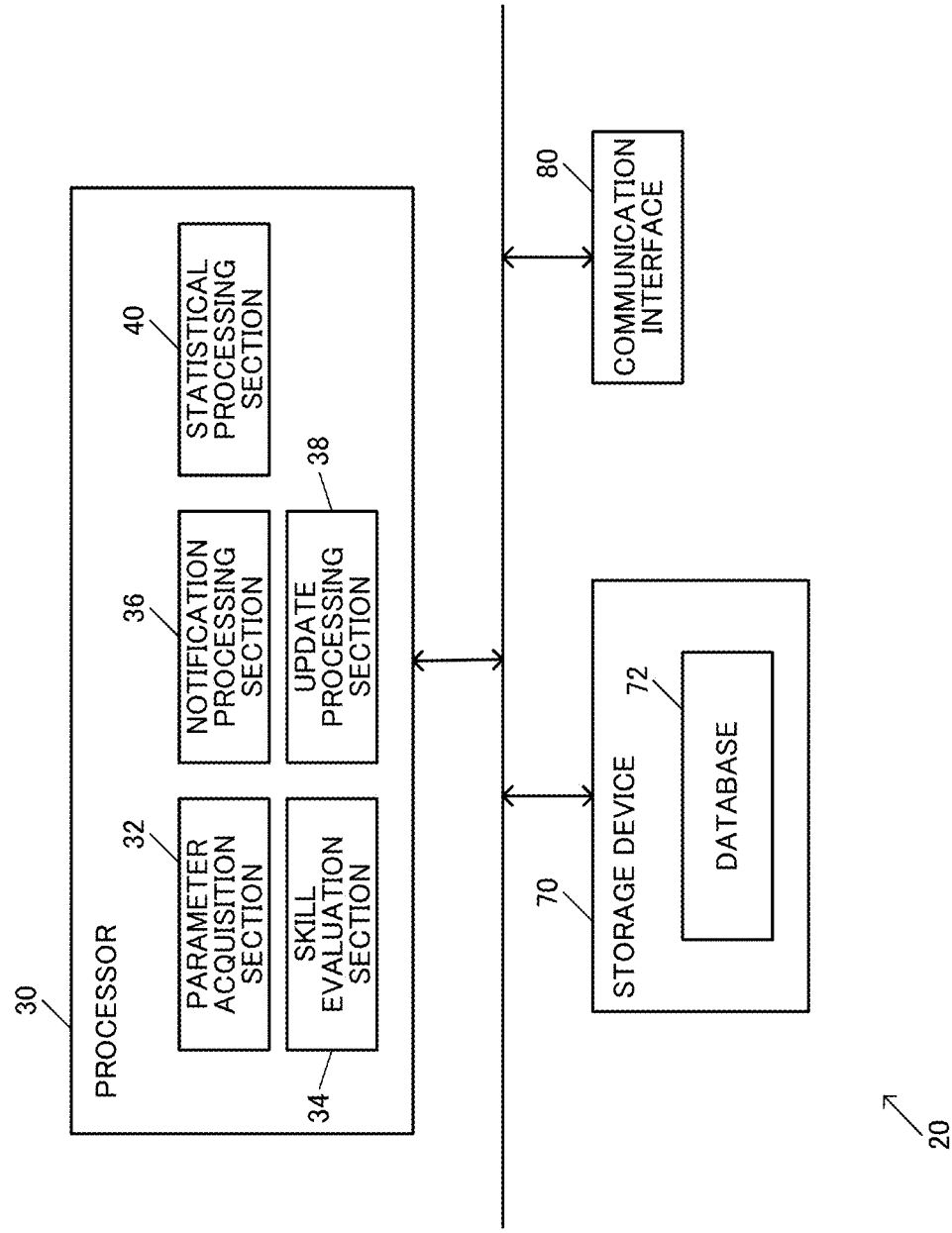
FIG. 7 shows a configuration example of an information processing system according to the present embodiment.

FIG. 7 shows a configuration example of the information processing system 20 according to the present embodiment. As shown in FIG. 7, the information processing system 20 includes a processor 30. Further, the information processing system 20 can include a storage device 70 and a communication interface 80. The information processing system 20 in FIG. 7 achieves, for example, the cloud server in FIG. 6.

The processor 30 includes hardware. The hardware of the processor 30 may be achieved by a digital circuit that processes a digital signal, or may be achieved by the digital circuit and an analog circuit that processes an analog signal. Also, the processor 30 may be achieved by one or more circuit devices (ICs) mounted on a circuit board or one or more circuit elements. Specifically, the processor 30 can be achieved by, for example, a CPU (Central Processing Unit). However, the processor 30 is not limited to the CPU, and may be achieved by various processors such as a GPU (Graphics Processing Unit) or a DSP (Digital Signal Processor). Further, the processor 30 may be achieved by a hardware circuit by ASIC.

The storage device 70 is a device for storing information, for example, a memory. The storage device 70 stores a database 72. The database 72 accumulates and stores information transmitted from each hospital, the training course providing organization, or the like in FIG. 6, for example. The storage device 70, which is a storage section, can be achieved by a semiconductor memory such as SRAM or DRAM. Alternatively, the storage device 70 may be achieved by a magnetic storage device such as a hard disk device (HDD), or may be achieved by an optical storage device. The storage device 70 functions as, for example, a work area for processing executed by the processor 30. For example, the storage device 70 stores computer-readable instructions, and for example, when the instructions are executed by the processor 30, processing of each section in the information processing system 20 is achieved. The instruction herein may be an instruction set for constituting the program, or may be an instruction for instructing the hardware circuit of the processor 30 to operate.

The processor 30, which is a processing section, includes a parameter acquisition section 32, a skill evaluation section 34, and a notification processing section 36. Further, the processor 30 can include an update processing section 38 and a statistical processing section 40.

The communication interface 80 communicates with an external device. The communication interface 80, which is a communication section, can be achieved by hardware such as a communication ASIC or a communication processor, communication firmware, and the like. For example, the communication interface 80 is communicated and connected to an external device such as an information processing device of the hospital or an information processing device of the training course providing organization in FIG. 6 via a network. The information processing device is achieved by a server, a PC (personal computer), or the like. The network is, for example, a communication path using the Internet, wireless LAN, and the like, and can include a dedicated line for direct connection and a LAN by Ethernet (registered trademark) as well as a telephone communication network, a cable network, a communication network such as a wireless LAN, and the like.

Figure 8:
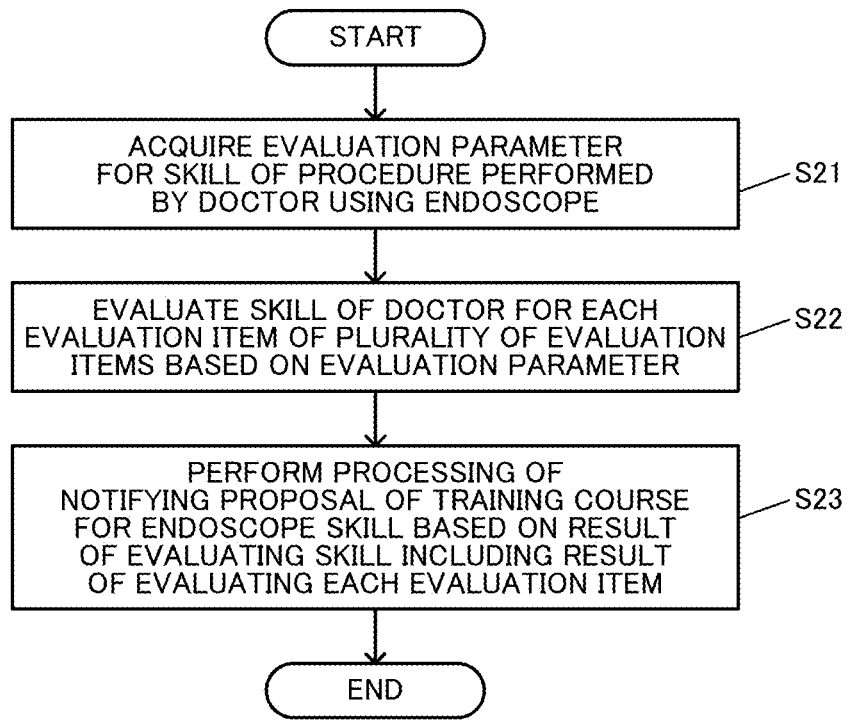
FIG. 8 shows a flow illustrating a process according to the present embodiment.

FIG. 8 shows a flow illustrating a process according to the present embodiment. As shown in FIG. 8, the processor 30 including the hardware acquires an evaluation parameter for evaluating the skill of a procedure performed by a doctor using an endoscope (step S21). The parameter acquisition section 32 performs the process of acquiring this evaluation parameter. For example, the processor 30 (parameter acquisition section 32) acquires evaluation parameters (parameter values) by receiving information on evaluation parameters from the information processing device of each hospital via the communication interface 80. For example, the processor 30 may acquire the operation data input by the doctor using the operation device of the endoscope as the information on evaluation parameters. The Skill is a skill acquired by a doctor performing a procedure. The evaluation parameter is a parameter that is prepared in advance by the system for evaluating the skill of the procedure performed by the doctor, and that numerically represents, for example, whether the doctor's skill is high or low.

Next, the processor 30 evaluates the skill of the doctor for each evaluation item of the plurality of evaluation items based on the acquired evaluation parameters (step S22). The skill evaluation section 34 evaluates this skill. For example, the system prepares a plurality of evaluation items for evaluating the skill of the doctor in advance. For example, as shown in FIG. 5, an evaluation item for endoscope insertion, an evaluation item for accuracy of treatment, an evaluation item for quickness of treatment tool operation, an evaluation item for stability of field of view, an evaluation item for utilization of air supply suction, or the like are prepared. Then, the processor 30 performs processing of evaluating the doctor's skill for each of these plurality of evaluation items based on the evaluation parameters acquired for the procedure performed by the doctor using the endoscope. For example, in FIG. 5, if the time t1 for the endoscope insertion, which is an evaluation parameter, is short, it is determined that the doctor's skill is high in the evaluation item for the endoscope insertion. In addition, if the positioning of the endoscope is accurate or the bleeding amount during the procedure is small, it is determined that the doctor's skill is high in the evaluation item for the accuracy of treatment. Further, if the time t3 and t5 for insertion of the cannula, the guide wire, or the like is short, it is determined that the doctor's skill is high in the evaluation item for the quickness of treatment tool operation. In addition, if a blurring amount of the endoscope image is small when positioning or cannulating the endoscope, it is determined that the doctor's skill regarding the stability of field of view of the endoscope is high. Additionally, if the air supply suction is successfully performed in a situation where the air supply suction is effective, it is evaluated that the doctor's skill for the utilization of air supply suction is high. Whether the skill is high or low may be determined by comparing with a reference value such as an average value of a doctor.

Next, the processor 30 performs processing of notifying a proposal of a training course for an endoscope skill based on a result of evaluating the skill including a result of evaluating each evaluation item (step S23). This processing of notifying is performed by the notification processing section 36. For example, based on the information accumulated in the database 72, the correlation between the result of evaluating the skill and the training course is specified as described in FIG. 6. This makes it possible to notify the doctor of the proposal of an appropriate training course according to the result of evaluating the skill of the doctor.

As described above, in the present embodiment, the evaluation parameters of the skill in the doctor's procedure are acquired, the skill of the doctor in each evaluation item is evaluated based on the evaluation parameters, and the processing of notifying a proposal of a training course is performed based on the result of evaluating the skill. By doing so, an appropriate training course according to the evaluation parameters when the doctor has performed the procedure is selected, and the doctor can be proposed to take the training course. Therefore, doctors can take effective training courses to improve skills in their weaknesses and skills that they need, and improve their skills, and it becomes possible to achieve the information processing system 20 that can efficiently recommend a training course that is effective for improving skills in a doctor's procedure.

For example, manufacturers and hospitals provide training courses to improve skills for procedures using an endoscope. The training courses may include various training courses such as cannulation training, drainage training, biliary duct stenting training, upper gastrointestinal endoscope training, colonoscopy training, endoscope angle operation training, and training for each technique such as ERCP. Also, training methods may include various modes such as training using an endoscope training simulator using virtual reality technology, training using a training model capable of inserting an endoscope, classroom training, or training by implementation training under the supervision of an instructor.

However, there are many types of procedures using an endoscope such as a flexible endoscope, thus resulting in a wide variety of treatment procedures. Therefore, there is a need for a system that encourages individuals to take appropriate training courses that specialize in procedures and operations that they are not good at. In this regard, the above-mentioned Japanese Patent Application Laid-Open No. 2019-197436 evaluates a skill level when inserting an endoscope, but does not disclose the viewpoint of proposing a recommended training course. Further, the prior art of Japanese Patent Application Laid-Open No. 2013-69251 evaluates a skill related to the driving technique of a car, but does not disclose the viewpoint of proposing a recommended training course. On the other hand, according to the present embodiment, skill evaluation can be performed based on the evaluation parameters acquired after the doctor performs the procedure to introduce a training course that is highly related to operations that doctors are not good at, and thus it becomes possible to efficiently notify a training course that is effective for improving the skill of a procedure that doctors are not good at or have little experience with.

In the present embodiment, a processing method for acquiring an evaluation parameter to evaluate a skill of a procedure performed by a doctor using an endoscope, evaluating the skill of the procedure performed by the doctor with respect to each evaluation item of a plurality of evaluation items, based on the evaluation parameter, and performing processing of notifying a proposal of a training course for an endoscope skill based on a result of evaluating the skill including a result of evaluating each evaluation item, can be achieved. According to such a processing method (a method of providing a training course), it becomes possible to achieve a processing method that can efficiently recommend a training course that is effective for improving the skill of a doctor's procedure.

Further, in step S23 of FIG. 8, the processor 30 performs processing of notifying for proposing a training course associated with an evaluation item having a low evaluation among a plurality of evaluation items. The low evaluation item indicates an evaluation item that is judged to be lower than the average, lower than other evaluation items, or lacking in technology compared to other evaluation items. For example. This processing of notifying is performed by the notification processing section 36. For example, among the first to n-th evaluation items (n is an integer of 2 or more), if the evaluation of the i-th evaluation item (i is an integer satisfying $1 \leq i \leq n$) is determined to be lower than the evaluation of other evaluation items, processing of notifying is performed to propose (recommend) a training course associated with the i-th evaluation item. By doing so, the doctor performs the procedure, the skill is evaluated according to the evaluation parameters, and if it is determined that the evaluation of the i-th evaluation item is low, it becomes possible to propose a training course associated with the i-th evaluation item to the doctor. Therefore, when the doctor takes the proposed training course, it is possible to expect an increase in the evaluation in the i-th evaluation item, which was considered to be low, and thus possible to efficiently propose a training course for appropriately improving the skill. Here, the association between each evaluation item of the plurality of evaluation items and each training course for the plurality of training courses is performed based on the correlation between the result of evaluating the skill and the training course as described in FIG. 6. For example, by updating the database 72 with information accumulated in the database 72, the correlation between the result of evaluating the skill and the training course is specified, and each evaluation item and each training course are associated with each other. In an initial state, each evaluation item and each training course may be associated with each other based on initial settings. The processor 30 is configured to access the storage device 70 that stores the database 72 that associates the evaluation item and the training course with each other, and perform processing of updating the database 72 based on the skill evaluated regarding the doctor who has taken the training course proposed.

Further, as shown in FIG. 7, the information processing system 20 includes the storage device 70 that stores the database 72 for associating a result of evaluating each evaluation item with a training course. Then, the processor 30 updates the database 72 based on the result of evaluating each evaluation item for the doctor who took the training course. This update process is performed by the update processing section 38. For example, the storage device 70 stores the database 72 containing information for associating the result of evaluating each evaluation item with the training course. This information is, for example, information on a weighting coefficient as described later. Then, the information in the database 72 is updated based on the result of evaluating each evaluation item for the doctors who took the training course. For example, the result of evaluating each evaluation item before and after taking the training course are compared, and the information in the database 72 is updated based on the result of the comparison. By doing so, the database 72 is updated based on the result of evaluating each evaluation item of the doctor who took the training course, and thus the association between the result of evaluating each evaluation item and the training course in the database 72 is also updated. Therefore, based on the database 72 that is updated according to the result of evaluating the skill of the doctor in each evaluation item, it becomes possible to select and propose an appropriate training course for improving each evaluation item, and becomes possible to efficiently recommend a training course that is effective for improving the skill of the doctor's procedure.

Figure 9:
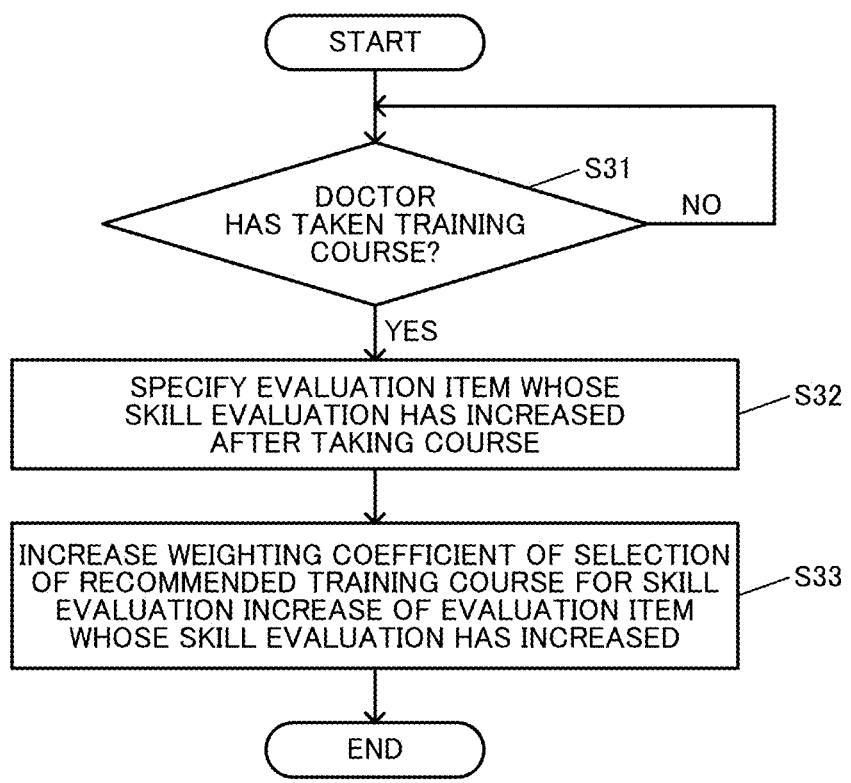
FIG. 9 shows a flow illustrating a database update process.

For example, it is assumed that a doctor takes a training course, and after taking the course, the skill evaluation in the i-th evaluation item (i is an integer satisfying $1 \leq i \leq n$) among the first to n-th evaluation items (n is an integer of 2 or more), which are a plurality of evaluation items, has increased. In this case, the processor 30 performs an update process for increasing the weighting coefficient of the selection of the recommended training course for the skill evaluation increase of the i-th evaluation item. This update process is performed by the update processing section 38. FIG. 9 shows a flow illustrating this update process. First, it is determined whether the doctor has taken the training course (step S31), and if so, the processor 30 specifies an evaluation item whose skill evaluation has increased after taking the course (step S32). Then, the processor 30 increases the weighting coefficient of the selection of the recommended training course for the skill evaluation increase of the evaluation item whose skill evaluation has increased (step S33).

By doing so, the database 72 is updated based on the change in the skill evaluation in each evaluation item before and after taking the training course. Then, when the skill evaluation of the i-th evaluation item increases by taking the training course, the weighting coefficient of the selection of the recommended training course for the skill evaluation increase of the i-th evaluation item increases, and thus the training course is likely to be selected as a training course that increases the i-th evaluation item. This makes it possible to appropriately propose training courses that are effective in increasing each evaluation item.

For example, if it is determined that the skill evaluation in the first evaluation item among the first to n-th evaluation items has increased from taking the training course by the doctor, the weighting coefficient of the selection of the recommended training course for the skill evaluation increase in the i-th evaluation item is increased. The weighting coefficient of the selection is set for each training course for the plurality of training courses in association with each evaluation item of the plurality of evaluation items. For example, for the k-th training course (k is an integer satisfying 1≤k≤m) among the first to m-th training courses (m is an integer of 2 or more), the first to n-th weighting coefficients for the first to n-th evaluation items are set. Then, when it is determined that the skill evaluation in the i-th evaluation item has increased from taking the k-th training course by the doctor, the i-th weighting coefficient of the first to n-th weighting coefficients associated with the k-th training course is increased. By doing so, for doctors who are determined to have a low i-th evaluation item, the probability that the k-th training course with an increasing weighting coefficient for the i-th evaluation item is selected and proposed is high. This makes it possible to appropriately propose a training course that is effective in increasing the i-th evaluation item. The processor 30 is configured to update by increasing the weighting coefficient of selection of the training course proposed when the evaluation item of the skill evaluated regarding the doctor who has taken the training course proposed is larger than the evaluation item of first skill evaluated.

Figure 10:
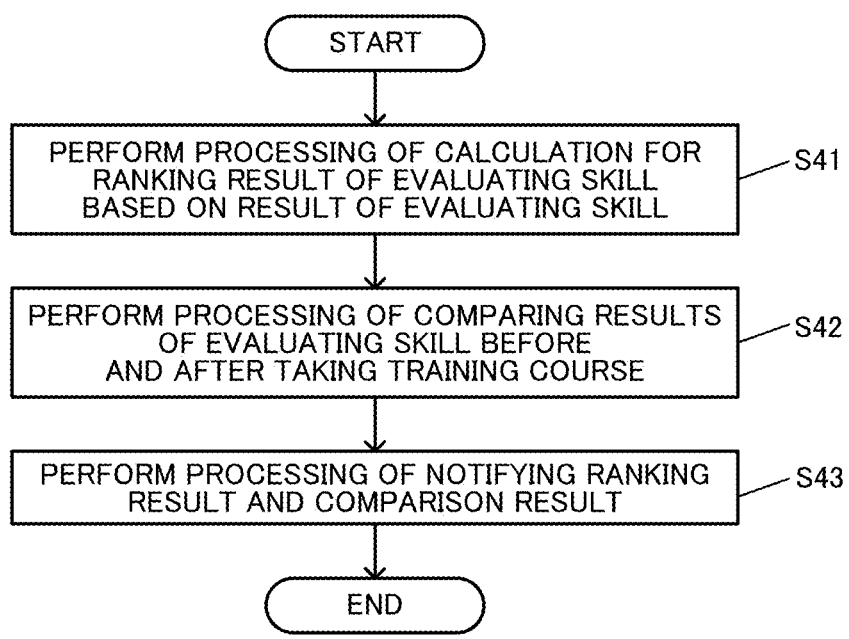
FIG. 10 shows a flow illustrating a process of calculation for ranking, and a process of comparing results of evaluating a skill.

FIG. 10 shows a flow illustrating another processing example according to the present embodiment. As shown in FIG. 10, the processor 30 performs processing of calculation for ranking the result of evaluating the skill based on the result of evaluating the skill (step S41). This processing of calculation for this ranking is performed by, for example, the statistical processing section 40. Also, the processor 30 performs processing of comparing the results of evaluating the skill of the doctor before and after taking the training course (step S42). This processing of comparing is performed by, for example, the statistical processing section 40. Then, the processor 30 performs processing of notifying the ranking result and the comparison result (step S43). This processing of notifying is performed by the notification processing section 36. The processor 30 is configured to perform processing of calculation for the ranking of the first skill evaluated by comparing the first skill with a plurality of evaluated skill stored or the first skill with average value in the database 72, and perform processing of notifying the ranking calculated.

As described above, in FIG. 10, based on the result of evaluating the skill, the processor 30 performs processing of calculation for ranking of the result of evaluating the skill, and performs processing of notifying the ranking result. For example, statistical processing for the result of evaluating the skill of the doctor who has undergone the processing of evaluating the skill based on the evaluation parameter is performed, and statistical processing for acquiring rankings, average values, and the like of result of evaluating the skill is performed by the statistical processing section 40. Then, the ranking result, the comparison result with respect to the average value, and the like are notified to each doctor by the notification processing section 36. By doing so, doctors will be able to understand the position of their skills in the evaluation items among all doctors. And, for example, in order to improve skills with low ranking, doctors will be more willing to take the proposed training courses, which can improve their motivation. This makes it possible to improve the skills of the entire doctor.

Further, in FIG. 10, the processor 30 performs processing of comparing the results of evaluating the skill of the doctor before and after taking the training course, and performs processing of notifying a comparison result. For example, the result of evaluating the skill before taking the training course and the result of evaluating the skill after taking the training course are compared, and processing of notifying is performed to notify the doctor of changes in skills of each evaluation item before and after taking the training course. For example, by taking the training course proposed last time, processing of notifying is performed to notify how the skill has changed in the target evaluation item. In the processing of notifying in this case, for example, the doctor is notified of the training course taken, the date of taking the course, and the information for making the doctor aware of how the evaluation of each evaluation item has changed before and after taking the training course. By doing so, the doctor can know the effect of the training course taken by observing the change in the skill of the evaluation item before and after taking the training course. Therefore, it is possible to give doctors an effective motivation to take a training course.

Further, examples of procedures performed by a doctor using an endoscope in the present embodiment include ERCP, EMR, ESD, EST, EPBD, ERBD, or TUL. ERCP is called endoscopic retrograde cholangiopancreatography and is the procedure described in FIG. 2 above. EMR stands for Endoscopic Mucosal Resection, and is a procedure for using an endoscope to widely excise the mucosal layer at the depth of the submucosal layer and recovering the tissue without damaging the muscle layer and below. ESD stands for Endoscopic submucosal dissection, and is a procedure for incising the entire circumference of the lesion with a special electric knife and then peeling off the lesion. EST stands for Endoscopic Sphincterotomy, and is a procedure for incising the papillary portion with an electric knife inserted through an endoscope for the purpose of widening the opening of the duodenal papilla. EPBD stands for Endoscopic Papillary Balloon Dilation, and is a procedure for placing a balloon dilator so as to straddle the papillary portion, and expanding the papillary portion by injecting physiological saline or the like into the balloon to inflate it. ERBD stands for Endoscopic Retrograde Biliary Drainage, and is a procedure for performing drainage such as stent placement in the biliary duct on the liver side from the duodenal papilla through the stenosis/occlusion site. TUL stands for Transurethral Ureterolithotripsy, and is a procedure for inserting an endoscope retrogradely from the urethra to the ureter, and crushing stones by a laser while checking the stones with the endoscope.

Such procedures such as ERCP, EMR, ESD, EST, EPBD, ERBD, and TUL are difficult procedures for doctors and require skills. In this regard, in the present embodiment, evaluation parameters for evaluating the skills of these procedures are acquired, the doctor's skills are evaluated based on the evaluation parameters, and a training course for endoscope skills is proposed. Therefore, doctors would be able to efficiently acquire difficult procedures such as ERCP, EMR, ESD, EST, EPBD, ERBD, and TUL by improving their skills in each evaluation item from taking the proposed training course.

Further, in the present embodiment, the procedure performed by the doctor using the endoscope is, for example, as shown in FIG. 2, a procedure including at least one of an endoscope insertion step, an endoscope positioning step, a cannulation step, a contrast radiography step, a guide wire insertion step, a guide wire removing step, and a treatment tool insertion step. Such a procedure requires a high skill of the doctor in the step of the procedure. Therefore, based on the skill evaluation parameters at that step, by evaluating the skills of the doctor and proposing an appropriate training course for improving the skills, it becomes possible for the doctor to properly acquire the procedure including such a step.

Further, the endoscope used for the procedure in the present embodiment may be an endoscope in which an endoscopic operation, which is at least one of forward/backward movement of an insertion section, a curving angle of a curving section of the insertion section, or rolling rotation of the insertion section, is electrically driven, as described later. In this case, the processor 30 acquires evaluation parameters based on operation data of the endoscope which is electrically driven. Alternatively, the processor 30 may acquire evaluation parameters based on the operation data of the endoscope and the endoscope image. When using an endoscope in which the endoscopic operation is electrically driven in this way, since evaluation parameters can be acquired based on the operation data of the endoscope which is electrically driven, there is an advantage that it is easy to acquire the evaluation parameters for evaluating the skill of the doctor's procedure. For example, in such an endoscope, based on the operation data input by the operator using an operation device (controller), endoscopic operations such as forward/backward movement of an insertion section, a curving angle of a curving section of the insertion section, or rolling rotation of the insertion section are electrically driven. Therefore, the processor 30 can acquire this operation data as information on evaluation parameters and easily evaluate the skill of the doctor's procedure. For example, data showing time required for each step of the procedure, air supply suction time, air supply suction amount, quickness of treatment tool operation, and accuracy of treatment can be easily acquired based on the operation data of the doctor when the endoscopic operation is electrically driven. Therefore, based on the evaluation parameters acquired based on the operation data, it becomes possible to evaluate the skill of the doctor's procedure and efficiently perform processing of proposing a training course. The procedure is related to the endoscope including the insertion section and the bending section. The endoscope is configured to electrically drive at least one of forward and backward movement of the insertion section, a bending angle of the bending section, or rolling rotation of the insertion section. The evaluation parameter acquired is an operation data of the endoscope electrically driven, the operation data including at least one of forward and backward movement of an insertion section, a bending angle of the bending section, or rolling rotation of the insertion section.

SPECIFIC EXAMPLES

Figure 11:
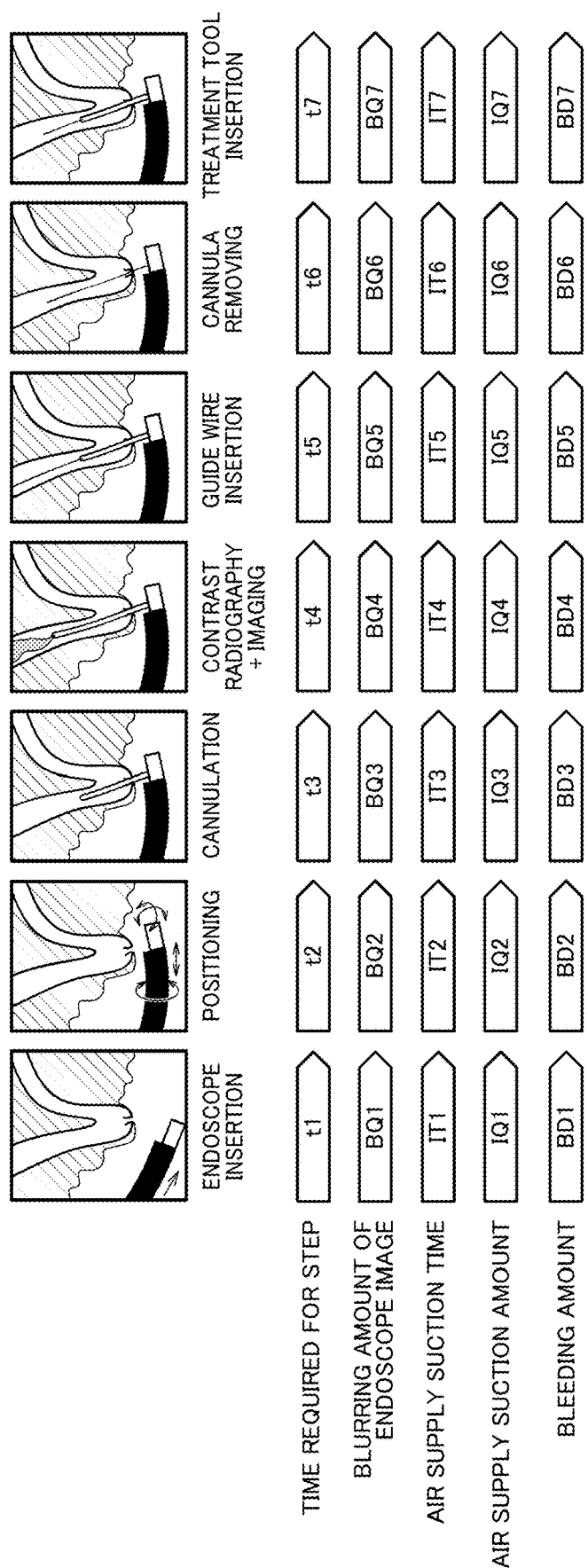
FIG. 11 is an explanatory diagram of a specific example of evaluation parameters.

Next, various specific examples of the present embodiment will be described. FIG. 11 is an explanatory diagram of a specific example of evaluation parameters.

In FIG. 11, time t1 to t7 required for each step of the procedure are acquired as evaluation parameters. The evaluation parameter of the time required for each step of the procedure may be acquired, for example, based on the operation data of the endoscopic operation, or by performing scene discrimination at each step based on an image (endoscope image) of the state of the procedure.

Further, in FIG. 11, blurring amounts BQ1 to BQ7 of the endoscope image at each step is acquired as evaluation parameters. The blurring amount of the endoscope image can be acquired by various processing. For example, the blurring amount can be acquired by performing matching processing between an endoscope image of a previous frame and an endoscope image of a current frame. Alternatively, the blurring amount of the endoscope image may be acquired by extracting the amplitude and frequency of vibrations in X and Y directions from the optical flow of the endoscope image.

The evaluation parameter can be acquired by matching processing between a first endoscope image and a second endoscope image acquired after the first endoscope image.

Also, in FIG. 11, air supply suction time IT1 to IT7 and air supply suction amount IQ1 to IQ7 are acquired as evaluation parameters. For example, in endoscopic procedures, since highly skilled doctors actively utilize air supply suction for efficient treatment, the usage time and the amount of air supply suction at each step can be acquired as evaluation parameters for the utilization of air supply suction. For example, when the air supply suction by an air supply suction pump is turned on and off based on the operation data of the doctor's air supply suction operation, the air supply suction time and the air supply suction amount can be acquired based on this operation data.

Further, in FIG. 11, bleeding amounts BD1 to BD7 in each step are acquired as evaluation parameters. The bleeding amount can be detected by extracting, for example, an increase or decrease in the area of a red region in the endoscope image. For example, in an endoscope image, a region where red pixels are aggregated is extracted as a bleeding region, and the bleeding amount is specified by the area of the bleeding region. For example, the bleeding amount can be used to evaluate a doctor's skill regarding the accuracy of treatment.

In addition, the skill of the doctor can be evaluated in terms of the number of approach trials to a treatment target, the number of operation trials of a treatment tool, the amount of forward/backward movement, and the like.

As described above, the evaluation parameter is, for example, a parameter of the time required for each step of the procedure. For example, the evaluation parameters are parameters of the time t1 to t7 in FIG. 11. Then, the processor 30 evaluates the skill regarding the evaluation item of the quickness of treatment based on the parameter of time which is an evaluation parameter. Referring to FIG. 5 as an example, as an evaluation item for the quickness of treatment, the skill of the doctor in the evaluation item for the endoscope insertion and the quickness of treatment tool operation is evaluated based on the parameter of time. By doing so, for example, it is evaluated that the shorter the time required for each step of the procedure, the higher the skill of the doctor regarding the quickness. If the time required for each step of the procedure is long, a training course to shorten this time is proposed to the doctor. This allows doctors to improve their skills in procedure quickness by taking the proposed training course and shortening the time required for each step.

Also, the evaluation parameter is, for example, a parameter of the blurring amount of the endoscope image when the procedure is performed. For example, the evaluation parameters are parameters of the blur amounts BQ1 to BQ7 in FIG. 11. Then, the processor 30 evaluates the skill regarding the evaluation item of the stability of field of view of the endoscope shown in FIG. 5, for example, based on the parameter of the blurring amount which is an evaluation parameter. By doing so, for example, it is evaluated that the smaller the blurring amount of the endoscope image in each step of the procedure, the more stable the field of view of the endoscope, and the higher the skill of the doctor regarding the stability of field of view. If the blurring amount of the endoscope image is large in each step of the procedure, a training course to reduce the blurring amount of the endoscope image is proposed to the doctor. This allows doctors to improve their skills in the stability of field of view by taking the proposed training course and reducing the blurring amount at each step.

Also, the evaluation parameter is a parameter of the air supply suction time or the air supply suction amount. For example, the evaluation parameters are parameters of the air supply suction time IT1 to IT7 and the air supply suction amounts IQ1 to IQ7 in FIG. 11. Then, the processor 30 evaluates the skill regarding the evaluation item of the utilization of air supply suction shown in FIG. 5, for example, based on the parameters of the air supply suction time or the air supply suction amount which is the evaluation parameters. By doing so, for example, if the air supply suction time or the air supply suction amount is appropriate, the skill of the doctor regarding the utilization of air supply suction is evaluated as high. If the air supply suction is not fully utilized in each step of the procedure, a training course to fully utilize the air supply suction is proposed to the doctor. This allows doctors to improve their skills in the utilization of air supply suction by taking the proposed training course.

Also, the evaluation parameter is, for example, a parameter of the bleeding amount when the procedure is performed. For example, the evaluation parameters are parameters of the bleeding amounts BD1 to BD7 in FIG. 11. Then, the processor 30 evaluates the skill regarding the evaluation item of the accuracy of treatment shown in FIG. 5, for example, based on the bleeding amount parameter which is an evaluation parameter. By doing so, for example, if the bleeding amount is small since the procedure is accurate at each step of the procedure, the skill of the doctor regarding the accuracy of treatment is evaluated as high. If the bleeding amount is large at each step of the procedure, a training course to reduce the bleeding amount is proposed to the doctor. This allows doctors to improve their skills in the accuracy of treatment by taking the proposed training course and reducing the bleeding amount.

For the evaluation item of the endoscope insertion in FIG. 5, the insertion time of the endoscope can be used as an evaluation parameter. For example, if the insertion time is longer than the average time or it takes much longer than that by the expert, it is determined that the endoscope insertion is immature. For the evaluation item of the quickness of treatment, the time from the start to the completion of incision and the time to remove stones can be used as evaluation parameters. For example, if the time from the start to the completion of incision is longer than the average time or it takes much longer than that by the expert, it is determined that the incision treatment is immature and the quickness of treatment is not sufficient. In addition, if the time to remove stones is longer than the average time or it takes much longer than that by the expert, it is determined that the stone removing treatment is immature and the quickness of treatment is not sufficient.

Further, for the evaluation item of the stability of field of view, the blurring amount can be used as an evaluation parameter as described above. In this case, it is determined whether the movement of the endoscope (field of view fluctuation) during the treatment is more than the average. For example, a highly skilled doctor operates the treatment tool without moving the endoscope (scope) after fixing the field of view to some extent. Therefore, if the field of view fluctuation during the treatment is larger than the average, it is considered that the endoscope is not stabilized during the treatment, and the skill in the stability of field of view is evaluated to be low.

Further, for the evaluation item of the utilization of air supply suction, the air supply suction time and the air supply suction amount can be used as evaluation parameters as described above. For example, a highly skilled doctor use techniques to attract or move away from organs by air suction or air supply rather than moving the endoscope when he/she wants to get closer to or look down away from a treatment target. Therefore, if the air supply suction time is compared with the average time or the time taken by the expert, and the use of air supply suction is low, it is determined that this technique cannot be utilized, and the skill in the utilization of air supply suction is evaluated to be low.

For the evaluation item of the accuracy of diagnosis, parameters such as what percentage of the organs could be imaged or whether all the landmarks of the organs could be imaged can be used as evaluation parameters. Then, the skill in the accuracy of diagnosis is evaluated by determining whether all the observation areas on the guideline can be imaged without overlooking the observation area in a limited time. In a case of gastric diagnosis, the landmarks are cardia, fundus, gastric corpus, pylorus, vestibular region, and pylorus, and it is evaluated whether all of them can be imaged. The landmarks can be identified by the difference and shape of the observed surface tissue.

Figure 12:
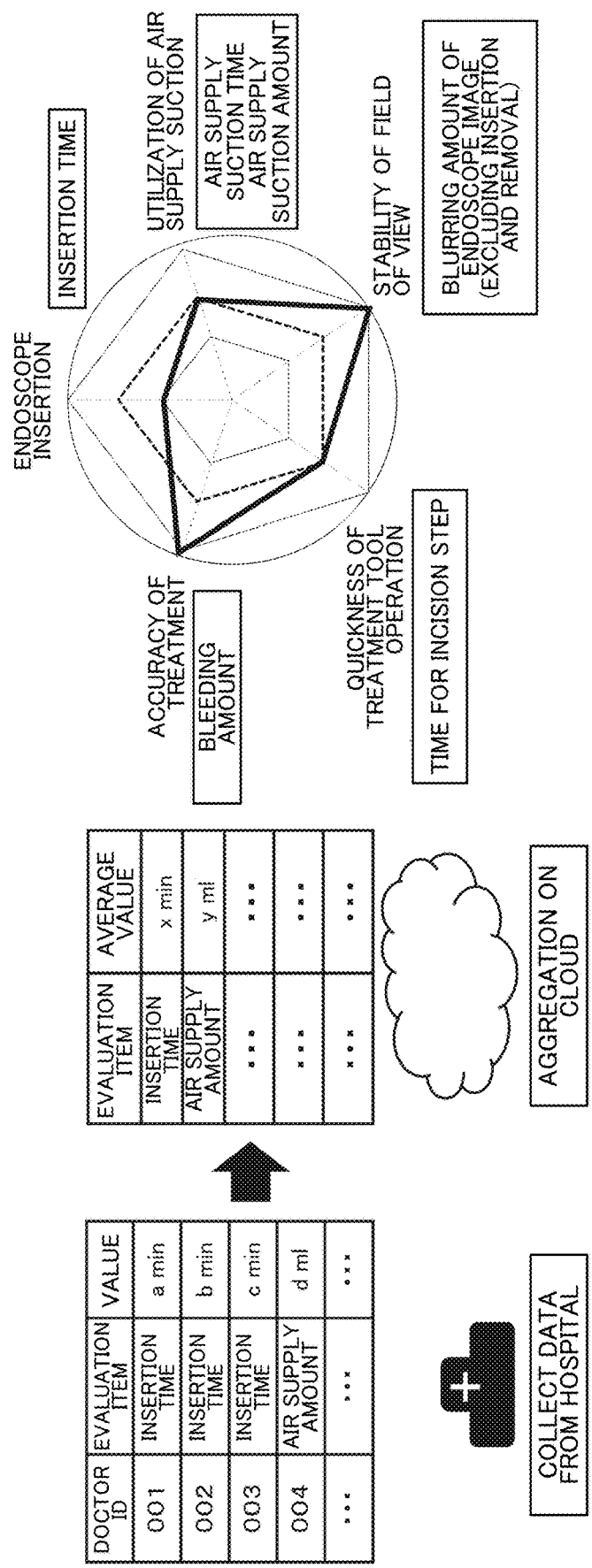
FIG. 12 is an explanatory diagram of a specific example of a process of evaluating skills of evaluation items.

FIG. 12 shows a specific example of evaluating skills based on evaluation parameters. For example, when a doctor performs a procedure in a hospital, values of the evaluation parameters for evaluation items such as insertion time and an air supply amount are acquired, and the values of these evaluation parameters are associated with the doctor's ID and collected from the hospital. Further, in the information processing system 20 which is a cloud server, the average value of the evaluation parameter values such as the insertion time and the air supply amount is aggregated and accumulated in the database 72. Then, the value of the evaluation parameter of the doctor is compared with the average value of other doctors accumulated in the database 72 and the value of an expert doctor, and the skill of the doctor is evaluated. For example, as shown in FIG. 12, the skill of the doctor is evaluated in evaluation items such as endoscope insertion, accuracy of treatment, quickness of treatment tool operation, stability of field of view, and utilization of air supply suction.

Figure 13:
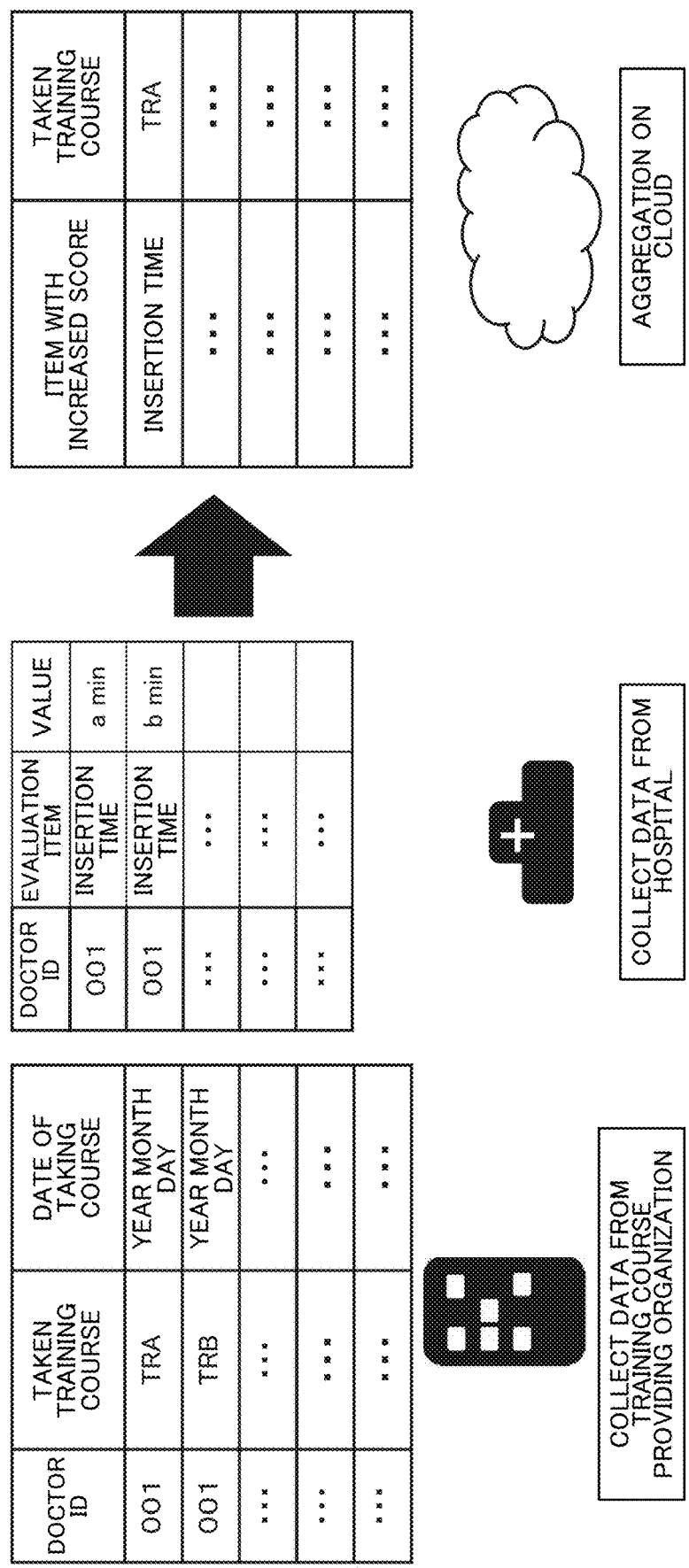
FIG. 13 is an explanatory diagram of a specific example of processing of notifying a training course.

FIG. 1 is an explanatory diagram of a specific example of processing of notifying a training course. As shown in FIG. 13, information on a history of taking a training course and date of taking the course is collected from the training course providing organization in association with the doctor's ID and accumulated in the database 72. In addition, the values of the evaluation parameters at each step of the procedure are collected from the hospital in association with the doctor's ID and accumulated in the database 72. As a result, the growth rate of the score, which is a result of evaluating the skill, can be calculated for each doctor's ID and accumulated in the database 72. Therefore, the information processing system 20, which is a cloud server, can create data in which the growth rate of the doctor's score and the history of taking the training course are associated with the doctor's ID. Then, based on this data, it becomes possible to select the most suitable training course for increasing the score, which is a result of evaluating the skill, and to propose it to the doctor.

Figure 14:
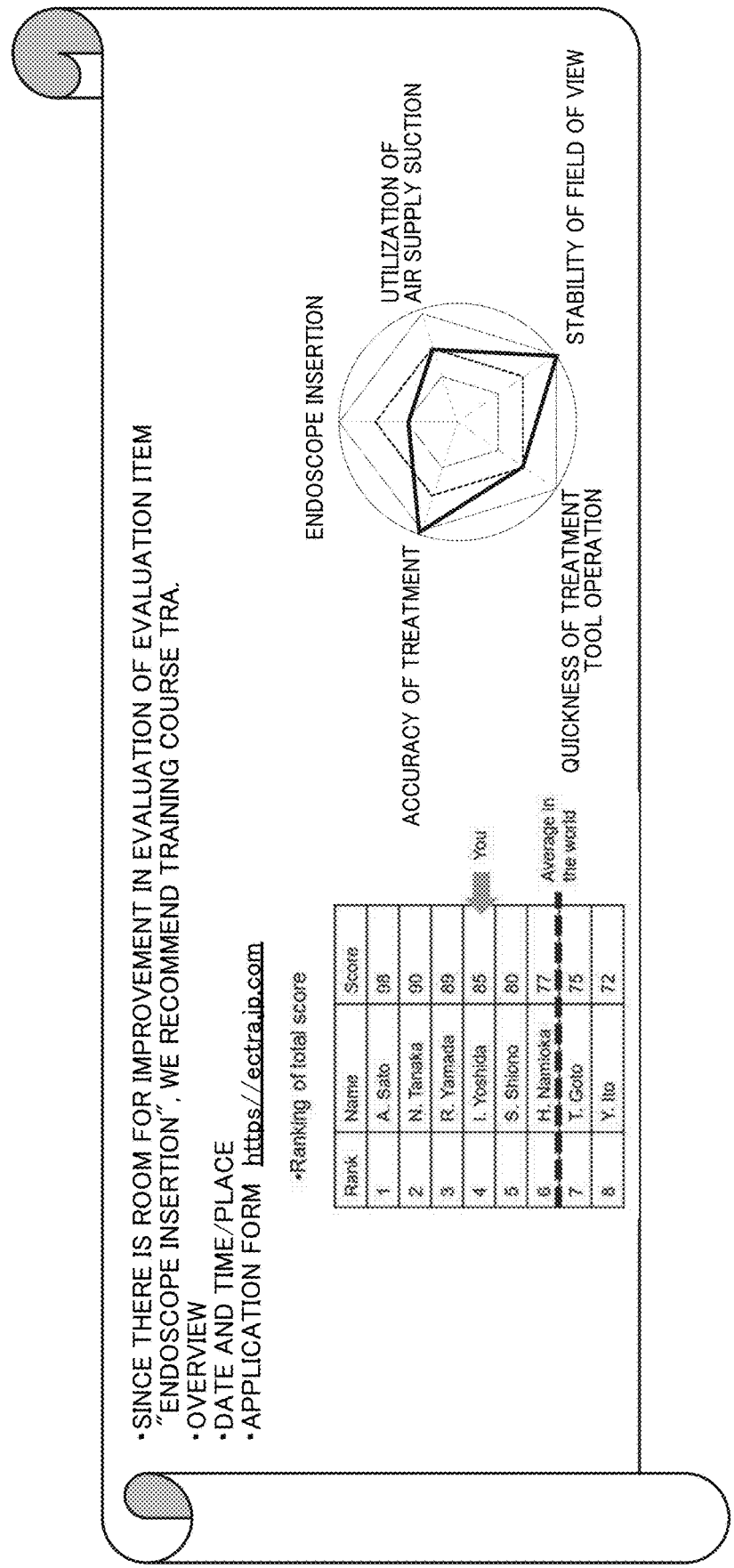
FIG. 14 shows a specific example of the notification.

FIG. 14 shows a specific example of the notification. In the notification of FIG. 14, since the evaluation of the endoscope insertion was low, the proposal of a training course suitable for improving the skill of the endoscope insertion is displayed. Further, in FIG. 14, date and time and place where the training course will be held and a link address of an application form are also displayed. Also, the result of evaluating a plurality of evaluation items and the ranking of the score, which is the result of evaluating the skill, are displayed. The ranking display also shows the ranking of the notified doctors and the average score. In this way, in FIG. 14, the ranking that visualizes where the score of oneself finally registered is in comparison with other people is displayed, and the ranking display leads to motivation for improvement. In the ranking display, instead of displaying the ranks of all people's scores, only a predetermined higher ranking may be displayed. Also, instead of the ranking, which area in the statistics you are in, such as "You are in the top 30%", may be displayed.

FIG. 15 also shows a specific example of the notification. In the notification of FIG. 15, the training course taken and the date of taking the course are displayed. In addition, the comparison result of evaluating the skill before and after taking the training course is displayed. The doctor who has received the notification can see the effect of the training course he/she took by looking at the comparison result. Therefore, doctors would seek to further improve their skills, and be able to effectively motivate them to take other training courses.

Endoscopic Operation by Electric Drive

Next, the endoscopic operation by electric drive will be described. As described above, when an endoscope whose endoscopic operation is electrically driven is used, evaluation parameters can be easily acquired by using the operation data of the endoscope.

When cannulation into the biliary duct is performed, it is performed by referring to an endoscope image showing the papillary portion. As described with reference to FIGS. 3 and 4, there are various forms of papillary portion and luminal tissue, and it is difficult to specify the insertion position and insertion direction of the cannula from the endoscope image.

On the other hand, the operator estimates the position of the opening and the travelling direction of the biliary duct based on past cases, experiences, and the like while viewing the endoscope image, and tries to insert the cannula from the opening into the biliary duct according to the estimation. At this time, in order to more accurately estimate the position of the opening and the travelling direction of the biliary duct, it is desirable that the position of the papillary portion in the image and the angle of view of the image are easy to compare with those in the past cases or are familiar to the operator.

As shown in FIG. 1, such positioning of the endoscope is performed by operating the distal end of the endoscope insertion section reaching the duodenum from outside the body. However, since the insertion section and the organ through which the insertion section passes are flexible, the operation performed at the base end of the insertion section is not easily transmitted to the distal end section. In addition, since the distal end section of the endoscope is not fixed to the duodenum and floats in the air, the distal end section of the endoscope is not stable with respect to the papillary portion, and the positional relationship between the distal end section and the papillary portion is not easily determined. For these reasons, it is difficult to adjust the position of the distal end section of the endoscope so that the field of view of the endoscope is facing directly front of the papillary portion or so that the papillary portion appears in the center of the field of view.

Therefore, in the present embodiment, the above-described positioning is automated by an electric medical system to assist the ERCP procedure. Further, by adding a configuration in which the insertion section of the endoscope is held in the duodenum, the electrically-driven force can be easily transmitted to the distal end section of the endoscope and the position of the distal end section can be desirably controlled. The details of this structure are described below.

Figure 16:
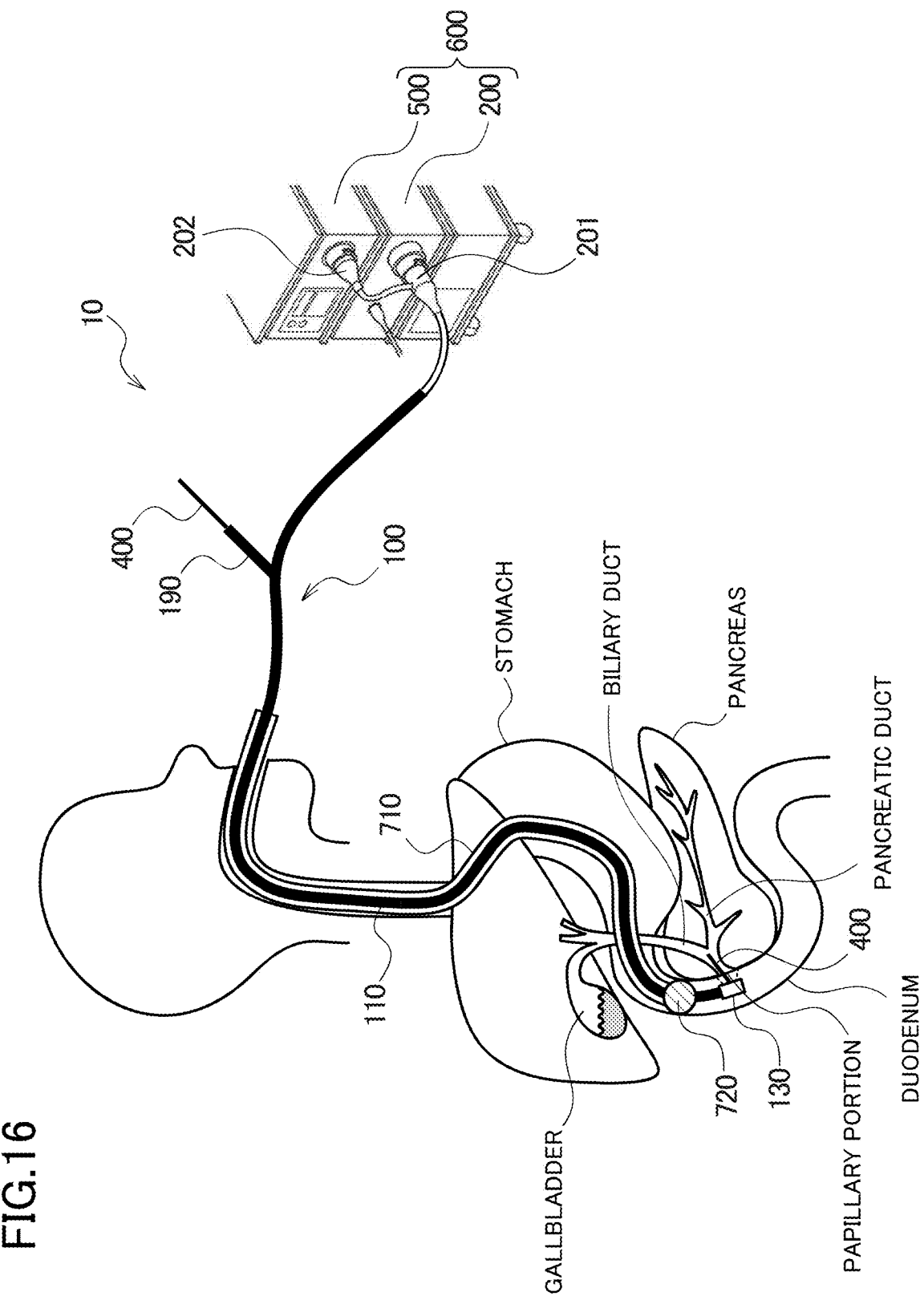
FIG. 16 shows a configuration example of a medical system according to the present embodiment.

FIG. 16 shows a configuration example of a medical system 10 according to the present embodiment. The medical system 10 includes an endoscope 100 and a control device 600. Further, the medical system 10 may include an overtube 710, a balloon 720, and a treatment tool 400. This medical system 10 is installed in each hospital, for example, in FIG. 6. The medical system 10 is also referred to as an endoscope system or an electric endoscope system.

The overtube 710 is a tube with a variable hardness that covers the insertion section 110 of the endoscope 100. The balloon 720 is provided near the distal end on the outer side of the overtube 710. When the endoscope 100 and the overtube 710 are inserted into the body, at least the curving section of the insertion section 110 is exposed from the distal end of the overtube 710. The curving section refers to a section structured to be bent at an angle corresponding to the curving operation in the vicinity of the distal end of the insertion section 110. The base end of the overtube 710 is present outside the body. The base end side of the insertion section 110 is exposed from the base end of the overtube 710.

An insertion opening 190 of the treatment tool is provided at the base end side of the insertion section 110, and a treatment tool channel for allowing the treatment tool 400 to pass through from the insertion opening 190 to the opening of the distal end section 130 is provided inside the insertion section 110. The insertion opening 190 of the treatment tool is also called a forceps opening; however, the treatment tool to be used is not limited to forceps.

The endoscope 100 is detachably connected to a control device 600 using connectors 201 and 202. The control device 600 includes a drive control device 200 to which the connector 201 is connected, and a video control device 500 to which the connector 202 is connected. The drive control device 200 controls the electrical driving of the endoscope 100 via the connector 201. Although not shown in FIG. 16, an operation device for manually operating the electrical driving may be connected to the drive control device 200. The video control device 500 receives an image signal from a camera provided at the distal end section 130 of the endoscope 100 via the connector 202, generates a display image from the image signal, and displays it on a display device (not shown). In FIG. 16, the drive control device 200 and the video control device 500 are shown as separate devices, but they may be structured as a single device. In this case, the connectors 201 and 202 may be integrated into a single connector.

Figure 17:
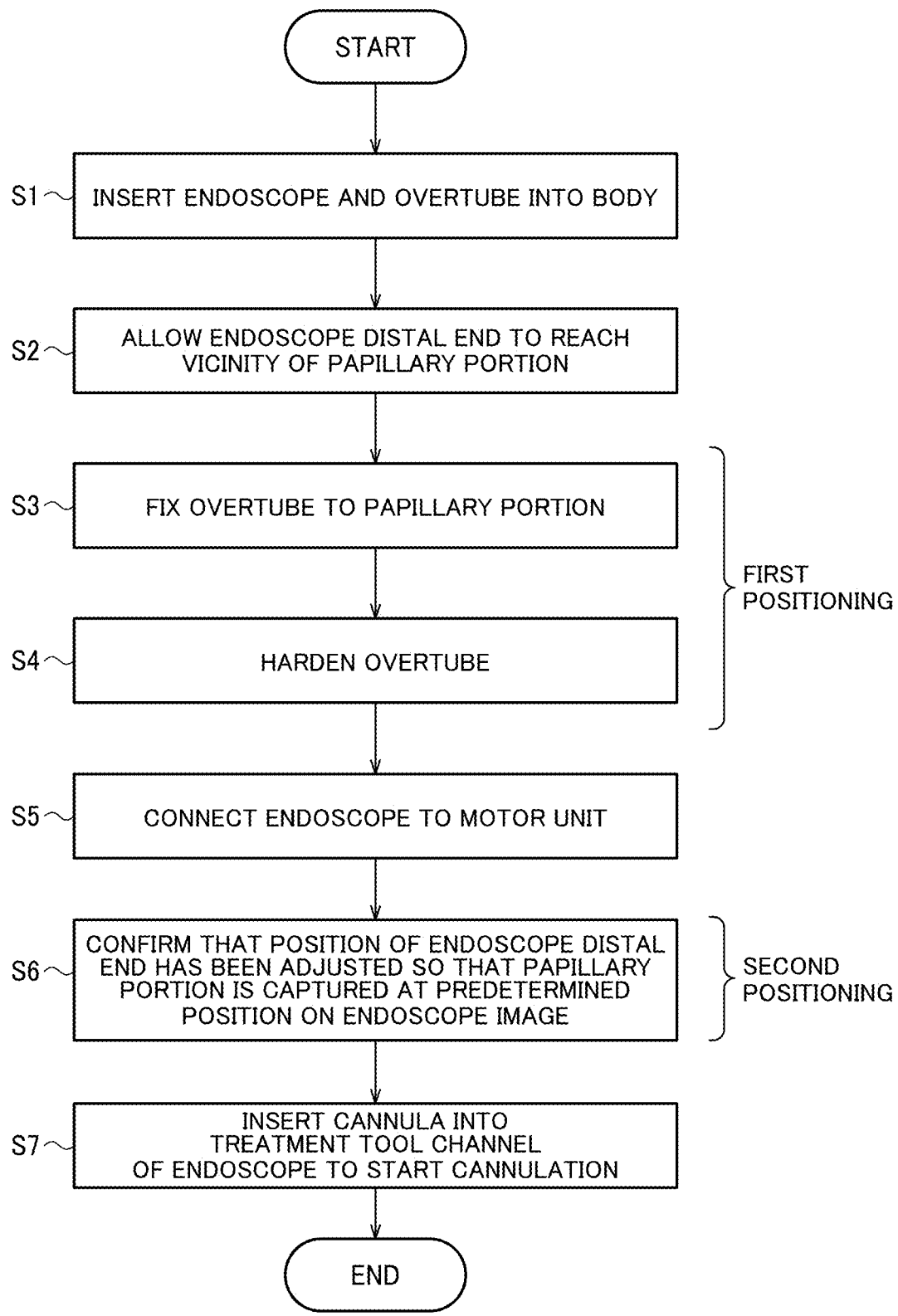
FIG. 17 shows a flow of the procedure in the present embodiment.

FIG. 17 shows a first flow of the procedure in the present embodiment. Here, an electric endoscope is assumed in which the forward and backward movement of the insertion section 110 of the endoscope 100, the curving of the curving section of the insertion section 110, and the rolling rotation of the insertion section 110 are electrically driven. However, it is sufficient that at least one of these functions is electrically driven. The term "electrical driving" means that the endoscope is driven by a motor or the like based on an electrical signal for controlling the endoscopic operation. For example, when the electrical driving is manually operated, an operation input to the operation device is converted into an electrical signal, and the endoscope is driven based on the electrical signal. For example, the operation data of the operation device is acquired by this electrical signal. In the following, the forward and backward movement may be simply referred to as "forward/backward movement".

In step S1, the operator inserts the insertion section 110 of the endoscope 100 and the overtube 710 into the duodenum. More specifically, in a state where the insertion section 110 is inserted into the overtube 710, the insertion section 110 and the overtube 710 are inserted into the duodenum together. The overtube 710, which is changeable in hardness, is soft in step S1. For example, the operator can move the insertion section 110 and the overtube 710 forward by a non-electrically-driven manual operation so that they are inserted into the body. The non-electrical driving means that the endoscope 100 is not electrically driven by a motor or the like, instead, the force applied to the operation section is directly transmitted to the endoscope by a wire or the like, thereby operating the endoscope. For example, in the present embodiment, steps S1 to S4 are not electrically driven. In this case, it is sufficient that at least the forward/backward movement is not electrically driven, and the curving, the rolling rotation, or both may be manually operated by electrical driving.

In step S2, the operator inserts the insertion section 110 until the distal end section 130 reaches the vicinity of the papillary portion. For example, when the operator manually inserts the insertion section 110 by non-electrical driving, the operator inserts the insertion section 110 until the papillary portion becomes visible in the endoscope image. At this point, the distal end of the endoscope 100 does not need to accurately reach the papillary portion; the distal end of the endoscope 100 may reach a position before the papillary portion or past the papillary portion.

In step S3, the operator fixes the distal end of the overtube 710 to the duodenum. As an example, the operator performs an operation to inflate the balloon 720 provided near the distal end of the overtube 710, and fixes the distal end of the overtube 710 to the duodenum by the balloon 720. In step S4, the operator performs an operation to harden the overtube 710. At this time, the overtube 710 is hardened while maintaining its shape in a state immediately before hardening, that is, the shape when it is inserted from the mouth to the duodenum. As a result, the insertion section 110 is held by the hardened overtube 710 and the balloon 720, thereby fixing the insertion route of the insertion section 110. These steps S3 and S4 are referred to as first positioning.

In step S5, the endoscope 100 is connected to the motor unit, and the non-electrical driving is switched to the electrical driving. The method of switching between the non-electrical driving and the electrical driving varies depending on the configuration of the drive mechanism. For example, in steps S1 to S4, the forward/backward movement may be non-electrically driven and the curving and the rolling rotation may be electrically driven. In this case, the forward/backward movement may be switched from the non-electrical driving to the electrical driving by connecting the endoscope 100 to the forward/backward drive device (not shown). Further, when the curving operation by non-electrical driving is enabled by providing a curving operation dial or the like capable of non-electrically performing the curving operation, the curving movement may be switched from the non-electrical driving to the electrical driving, for example, by connecting the connector 201 to the drive control device 200. Alternatively, even if the motor unit is kept connected, the motor may be structured to be detachable by a clutch mechanism or the like, and the non-electrical driving may be switched to the electrical driving by the clutch mechanism. Step S5 may be performed before step S1. For example, when the forward/backward movement is manually operated by electrical driving, the endoscope 100 may be connected to the motor unit before step S1.

In step S6, the drive control device 200 automatically positions the distal end section 130 at the papillary portion, and the operator confirms that the position of the distal end section 130 has been adjusted so that the papillary portion is captured at a predetermined position on the endoscope image. The drive control device 200 acquires an endoscope image from the video control device 500 and performs positioning of the distal end section 130 of the endoscope 100 based on the endoscope image. More specifically, the drive control device 200 controls the forward/backward movement, curving, or rolling rotation by electrical driving so that the papillary portion is captured at a position registered in advance on the endoscope image. The position registered in advance is, for example, the center of the image. More preferably, the positioning may be performed so that the opening of the luminal tissue is captured at a position registered in advance. Further, the drive control device 200 may perform electrical driving control based on the endoscope image so that the camera faces directly the front of the papillary portion or so that the papillary portion is captured at an appropriate angle of view. The drive control device 200 may also adjust the angle of view in imaging the papillary portion by controlling the diameter of the balloon 720 by electrical driving based on the endoscope image so that the distance between the camera and the papillary portion can be changed without changing the line-of-sight direction of the camera. This step S6 is referred to as second positioning.

In step S7, the operator inserts a cannula into the treatment tool channel through the insertion opening 190 to start cannulation into the biliary duct.

In FIG. 17, although the operation of the balloon in step S3 and the hardening of the overtube in step S4 are performed by non-electrical driving, they may be performed by electrical driving. In this case, the operator inputs an instruction from the operation device, and the drive control device 200 may inflate the balloon or harden the overtube by electrical driving using the instruction as a trigger. Alternatively, the drive control device 200 may perform an image recognition process for detecting the papillary portion from the endoscope image, and may automatically inflate the balloon or harden the overtube using the detection of the papillary portion from the endoscope image as a trigger.

According to the procedure flow described above, by inflating the balloon 720 before hardening the overtube 710 in step S3, the position of the distal end of the overtube 710 does not shift when the overtube 710 is hardened. Specifically, the distal end of the overtube 710 can be accurately positioned. In addition, by the first positioning in steps S3 and S4, the insertion route of the insertion section 110 is held by the balloon 720 and the overtube 710. As a result, in the second positioning in step S6, the forward/backward movement, curving, or rolling rotation of the endoscope 100 due to the electrical driving is easily transmitted from the base end side to the distal end of the insertion section 110.

Figure 18:
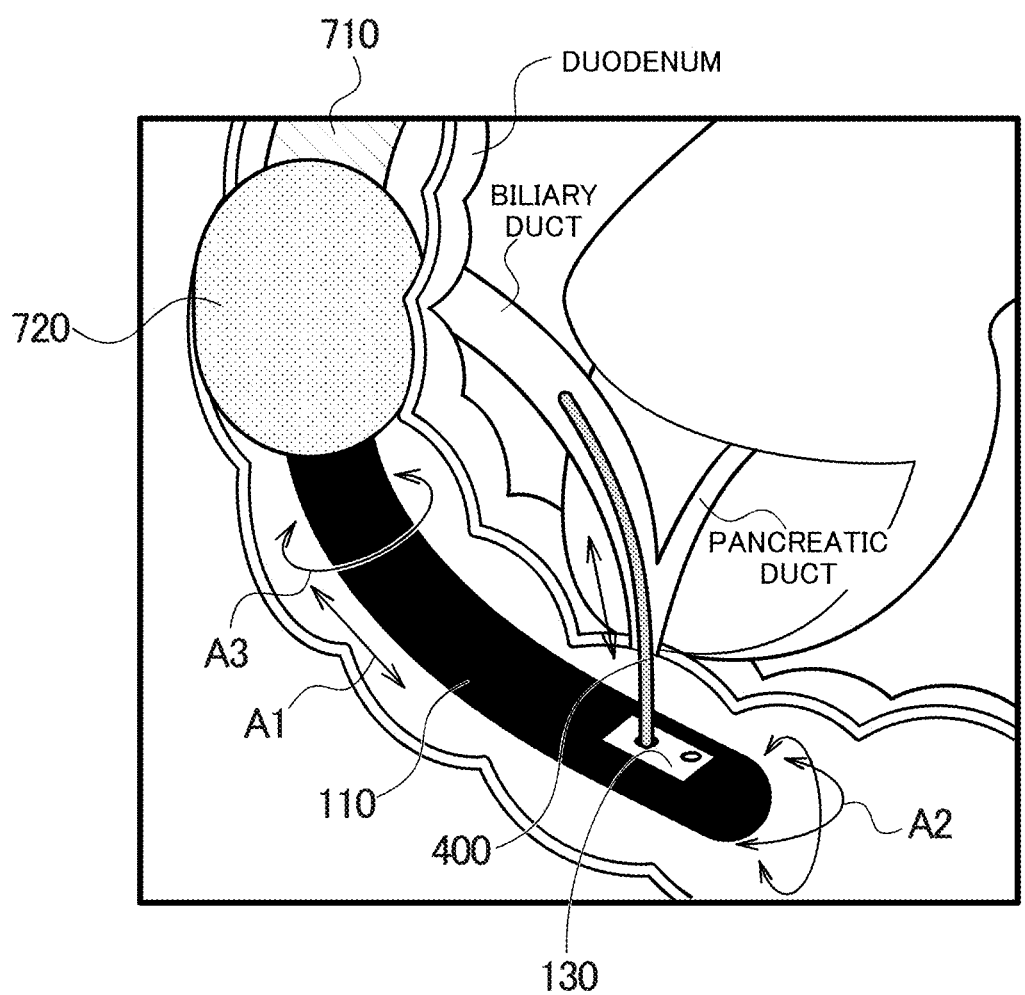
FIG. 18 shows the vicinity of a distal end of an endoscope positioned by an overtube and a balloon.

FIG. 18 shows the vicinity of the distal end of an endoscope positioned by the overtube 710 and the balloon 720. As shown in FIG. 18, the balloon 720 is fixed at a position slightly apart from the papillary portion to the pyloric side of the stomach. More specifically, the balloon 720 is positioned closer to the base end of the insertion section 110 than the base end of the curving section of the insertion section 110. By combining such a balloon 720 with the overtube 710 having a variable hardness, the curving section exposed to the papillary portion side from the balloon 720 and the distal end section 130 can be freely operated without being fixed, and the electrical driving from the base end side can be efficiently transmitted to the distal end section 130 of the endoscope.

The endoscopic operation by the electrical driving is the forward and backward movement shown in A1, a curving movement shown in A2, or the rolling rotation shown in A3. The forward movement is a shift toward the distal end side along the axial direction of the insertion section 110, and the backward movement is a shift toward the base end side along the axial direction of the insertion section 110. The curving movement is a movement by which the angle of the distal end section 130 is changed due to the bending of the bending section. The bending movement includes bending movements in two orthogonal directions, which can be controlled independently. One of the two orthogonal directions is referred to as the vertical direction and the other is referred to as the horizontal direction. The rolling rotation is a rotation about an axis of the insertion section 110.

FIG. 18 shows an example in which the balloon 720 is attached to the distal end of the overtube 710 and the endoscope protrudes from the distal end of the overtube 710. However, it is sufficient that the overtube 710 and the balloon 720 are configured so that a portion of the bending section beyond the base end can freely move. For example, it may also be arranged such that a soft tube with a constant hardness extends beyond the overtube with a variable hardness, and the balloon 720 is attached to the boundary thereof. In this case, although a part of the base end side of the bending section is covered with the soft tube, its movement is not hindered.

Although the embodiments to which the present disclosure is applied and the modifications thereof have been described above, the present disclosure is not limited to the embodiments and the modifications thereof, and various modifications and variations in elements may be made in implementation without departing from the spirit and scope of the present disclosure. The plurality of elements disclosed in the embodiments and the modifications described above may be combined as appropriate to form various disclosures. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

EXAMPLE

Example 1. An information processing system comprising a processor including hardware, the processor configured to:
acquire an evaluation parameter to evaluate a skill of a procedure performed by a doctor using an endoscope;
evaluate the skill of the procedure performed by the doctor with respect to each evaluation item of a plurality of evaluation items, based on the evaluation parameter; and
perform processing of notifying a proposal of a training course for an endoscope skill based on a result of evaluating the skill including a result of evaluating each evaluation item.

Example 2. The information processing system as defined in Example 1, wherein
the processor performs the processing of notifying the proposal of the training course associated with an evaluation item that is evaluated low among the plurality of evaluation items.

Example 3. The information processing system as defined in Example 1, further comprising a storage device that stores a database that associates the result of evaluating each evaluation item and the training course with each other,
wherein the processor performs processing of updating the database based on the result of evaluating each evaluation item regarding the doctor who takes the training course.

Example 4. The information processing system as defined in Example 3, wherein
the processor performs the processing of updating for increasing a weighting coefficient of selection of the training course recommended for skill evaluation increase of an i-th evaluation item when the doctor takes the training course, and after taking the training course, the skill evaluation in the i-th evaluation item (i is an integer satisfying $1 \leq i \leq n$) among first to n-th evaluation items (n is an integer of 2 or more), which are the plurality of evaluation items, is increased, Example 5. The information processing system as defined in Example 1, wherein
the processor performs processing of calculation for ranking the result of evaluating the skill based on the result of evaluating the skill, and performs the processing of notifying a ranking result.

Example 6. The information processing system as defined in Example 1, wherein
the processor performs processing of comparing the results of evaluating the skill of the doctor before and after taking the training course, and performs processing of notifying a comparison result.

Example 7. The information processing system as defined in Example 1, wherein
the evaluation parameter is a parameter of time required for each step of the procedure, and the processor evaluates the skill regarding an evaluation item of quickness of treatment based on the parameter of time.

Example 8. The information processing system as defined in Example 1, wherein
the evaluation parameter is a parameter of a blurring amount of an endoscope image when the procedure is performed, and
the processor evaluates the skill regarding an evaluation item of stability of field of view of the endoscope based on the parameter of the blurring amount.

Example 9. The information processing system as defined in Example 1, wherein
the evaluation parameter is a parameter of an air supply suction time or an air supply suction amount, and
the processor evaluates the skill regarding an evaluation item of utilization of air supply suction based on the parameter of the air supply suction time or the air supply suction amount.

Example 10. The information processing system as defined in Example 1, wherein
the evaluation parameter is a parameter of a bleeding amount when the procedure is performed, and
the processor evaluates the skill regarding an evaluation item of accuracy of treatment based on the parameter of the bleeding amount.

Example 11. The information processing system as defined in Example 1, wherein
the procedure is ERCP, EMR, ESD, EST, EPBD, ERBD or TUL.

Example 12. The information processing system as defined in Example 1, wherein
the procedure includes at least one of an endoscope insertion step, an endoscope positioning step, a cannulation step, a contrast radiography step, a guide wire insertion step, a guide wire removing step, and a treatment tool insertion step.

Example 13. The information processing system as defined in Example 1, wherein
the endoscope is an endoscope in which an endoscopic operation, which is at least one of forward and backward movement of an insertion section, a curving angle of a curving section of the insertion portion, or rolling rotation of the insertion section, is electrically driven, and
the processor acquires the evaluation parameter based on operation data of the endoscope which is electrically driven.

Example 14. A processing method, comprising:
acquiring an evaluation parameter to evaluate a skill of a procedure performed by a doctor using an endoscope;
evaluating the skill of the procedure performed by the doctor with respect to each evaluation item of a plurality of evaluation items, based on the evaluation parameter; and
performing processing of notifying a proposal of a training course for an endoscope skill based on a result of evaluating the skill including a result of evaluating each evaluation item.

What is claimed is:
1. An information processing system comprising:
a processor including hardware, the processor configured to:
acquire a plurality of endoscopic images acquired during an endoscopic operation;
perform at least one of matching processing between adjacent frames of the plurality of endoscopic images to extract an amplitude and frequency of vibrations from an optical flow of each of the plurality of endoscopic images;
calculate, as a first evaluation parameter, blurring amounts of the plurality of endoscopic images at each step of a plurality of predetermined steps of the endoscopic operation based on the amplitude and frequency of vibrations;
evaluate a value of a first skill of a doctor who performed the endoscopic operation based on the first evaluation parameter;
determine a proposed training course selected from a plurality of training courses relating to the first skill and stored in a database, wherein each of the plurality of training courses relating to the first skill is stored in association with a corresponding one of a first plurality of weighting coefficients, and wherein the proposed training course is selected based on the value of the first skill and the weighting coefficient associated with the proposed training course;
perform processing of notifying the proposed training course; and
perform processing of updating the database to change the weighting coefficient associated with the proposed training course after the proposed training course is taken.

2. The information processing system as defined in claim 1,
wherein the processor is configured to:
evaluate values of a plurality of skills of the doctor who performed the endoscopic operation, wherein the values of the plurality of skills includes the value of the first skill; and
determine the value of the first skill is a lowest value of the values of the plurality of skills; and
select the proposed training course based on a determination that the value of the first skill is the lowest value of the values of the plurality of skills and the weight coefficient associated with the proposed training course.

3. The information processing system of claim 1,
wherein the processor is configured to:
acquire a plurality of endoscopic images acquired during another endoscopic operation performed after the proposed training course is taken;
perform the at least one of matching processing between adjacent frames of the plurality of endoscopic images acquired during the another endoscopic operation to extract an amplitude and frequency of vibrations from an optical flow of each of the plurality of endoscopic images;
calculate, as an updated first evaluation parameter, blurring amounts of the plurality of endoscopic images at each step of a plurality of predetermined steps of the another endoscopic operation based on the amplitude and frequency of vibrations;
evaluate an updated value of the first skill of the doctor who performed the endoscopic operation based on the updated first evaluation parameter;
determine whether the updated value of the first skill is greater than the first value of the first skill; and
in response to determining that the updated value of the first skill is greater than the first value of the first skill, in performing the processing of updating the database, increase the weighting coefficient associated with the proposed training course to increase the likelihood that the proposed training course will be selected in the future.

4. The information processing system of claim 1, wherein the processor is configured to:
calculate a ranking of the value of the first skill evaluated among a plurality of values of the first skill stored in the database; and
perform processing of notifying the ranking calculated.

5. The information processing system of claim 3, wherein the processor is configured perform processing of notifying a result of the determination of whether the updated value of the first skill is greater than the first value of the first skill.

6. The information processing system of claim 1, wherein the endoscopic operation is endoscopic retrograde cholangiopancreatography (ERCP), endoscopic mucosal resection (EMR), endoscopic submucosal dissection (ESD), endoscopic sphincterotomy (EST), endoscopic papillary balloon dilation (EPBD), endoscopic retrograde biliary drainage (ERBD) or transurethral ureterolithotripsy (TUL).

7. The information processing system of claim 1, wherein the plurality of steps of the endoscopic operation comprises two or more of an endoscope insertion step, an endoscope positioning step, a cannulation step, a contrast radiography step, a guide wire insertion step, a guide wire removing step, and a treatment tool insertion step.

8. The information processing system according to claim 1,
wherein the processor is further configured to:
perform image processing to extract regions of aggregated red pixels in the plurality of endoscopic images;
calculate, as a second evaluation parameter, a bleeding amount in each step of the plurality of predetermined steps of the endoscopic operation based on the regions of aggregated red pixels extracted;
evaluate a value of a second skill of the doctor who performed the endoscopic operation based on the second evaluation parameter;
determine a proposed training course selected from a plurality of training courses relating to the second skill and stored in the database, wherein each of the plurality of training courses relating to the second skill is stored in association with a corresponding one of a second plurality of weighting coefficients, and wherein the proposed training course is selected based on the value of the second skill and the weighting coefficient associated with the proposed training course;
perform processing of notifying the proposed training course; and
perform processing of updating the database to change the weighting coefficient associated with the proposed training course after the proposed training course is taken.

9. The information processing system according to claim 8,
wherein the processor is further configured to:
image process the plurality of endoscopic images to perform scene discrimination at each of the plurality of predetermined steps of the endoscopic operation;
calculate, as a third evaluation parameter, a time required to perform each of the plurality of predetermined steps of the endoscopic operation based on the scene discrimination at each of the plurality of predetermined steps;
evaluate a value of a third skill of a doctor who performed the endoscopic operation based on the third evaluation parameter;
determine a proposed training course selected from a plurality of training courses relating to the third skill and stored in the database, wherein each of the plurality of training courses relating to the third skill is stored in association with a corresponding one of a third plurality of weighting coefficients, and wherein the proposed training course is selected based on the value of the third skill and the weighting coefficient associated with the proposed training course;
perform processing of notifying the proposed training course; and
perform processing of updating the database to change the weighting coefficient associated with the proposed training course after the proposed training course is taken.

10. The information processing system according to claim 9,
wherein the processor is further configured to:
receive operation data of the endoscopic operation;
calculate, as a fourth evaluation parameter, at least one of air supply suction time and air supply suction amount at each step of the plurality of predetermined steps of the endoscopic operation based on the operation data of the endoscopic operation;
evaluate a value of a fourth skill of the doctor who performed the endoscopic operation based on the fourth evaluation parameter;
determine a proposed training course selected from a plurality of training courses relating to the fourth skill and stored in the database, wherein each of the plurality of training courses relating to the fourth skill is stored in association with a corresponding one of a fourth plurality of weighting coefficients, and wherein the proposed training course is selected based on the value of the fourth skill and the weighting coefficient associated with the proposed training course;
perform processing of notifying the proposed training course; and
perform processing of updating the database to change the weighting coefficient associated with the proposed training course after the proposed training course is taken.

11. The information processing system according to claim 9,
wherein the processor is further configured to:
receive operation data of the endoscopic operation;
calculate, as a fourth evaluation parameter, at least one of forward and backward movement of an insertion section of an endoscope, a bending angle of a bending section of the endoscope, and rolling rotation of the insertion section of the endoscope at each step of the plurality of predetermined steps of the endoscopic operation based on the operation data of the endoscopic operation;
evaluate a value of a fourth skill of the doctor who performed the endoscopic operation based on the fourth evaluation parameter; and
determine a proposed training course selected from a plurality of training courses relating to the fourth skill and stored in the database, wherein each of the plurality of training courses relating to the fourth skill is stored in association with a corresponding one of a fourth plurality of weighting coefficients, and wherein the proposed training course is selected based on the value of the fourth skill and the weighting coefficient associated with the proposed training course;

perform processing of notifying the proposed training course; and perform processing of updating the database to change the weighting coefficient associated with the proposed training course after the proposed training course is taken.

12. A method implemented by a processor, the method comprising:

acquiring a plurality of endoscopic images acquired during an endoscopic operation;

performing at least one of matching processing between adjacent frames of the plurality of endoscopic images to extract an amplitude and frequency of vibrations from an optical flow of each of the plurality of endoscopic images;

calculating, as a first evaluation parameter, blurring amounts of the plurality of endoscopic images at each step of a plurality of predetermined steps of the endoscopic operation based on the amplitude and frequency of vibrations;

evaluating a value of a first skill of a doctor who performed the endoscopic operation based on the first evaluation parameter;

determining a proposed training course selected from a plurality of training courses relating to the first skill and stored in a database, wherein each of the plurality of training courses relating to the first skill is stored in association with a corresponding one of a plurality of weighting coefficient, and wherein the proposed training course is selected based on the value of the first skill and the weighting coefficient associated with the proposed training course;

performing processing of notifying the proposed training course; and performing processing of updating the database to change the weighting coefficient associated with the proposed training course after the proposed training course is taken.

13. The method according to claim 12, further comprising:

acquiring a plurality of endoscopic images acquired during another endoscopic operation performed after the proposed training course is taken;

performing the at least one of matching processing between adjacent frames of the plurality of endoscopic images acquired during the another endoscopic operation to extract an amplitude and frequency of vibrations from an optical flow of each of the plurality of endoscopic images;

calculating, as an updated first evaluation parameter, blurring amounts of the plurality of endoscopic images at each step of a plurality of predetermined steps of the another endoscopic operation based on the amplitude and frequency of vibrations;

evaluating an updated value of the first skill of the doctor who performed the endoscopic operation based on the updated first evaluation parameter;

determining whether the updated value of the first skill is greater than the first value of the first skill; and in response to determining that the updated value of the first skill is greater than the first value of the first skill, in performing the processing of updating the database, increasing the weighting coefficient associated with the proposed training course to increase the likelihood that the proposed training course will be selected in the future.

14. The method according to claim 12, further comprising:

performing image processing to extract regions of aggregated red pixels in the plurality of endoscopic images;

calculating, as a second evaluation parameter, a bleeding amount in each step of the plurality of predetermined steps of the endoscopic operation based on the regions of aggregated red pixels extracted;

evaluating a value of a second skill of the doctor who performed the endoscopic operation based on the second evaluation parameter;

determining a proposed training course selected from a plurality of training courses relating to the second skill and stored in the database, wherein each of the plurality of training courses relating to the second skill is stored in association with a corresponding one of a second plurality of weighting coefficients, and wherein the proposed training course is selected based on the value of the second skill and the weighting coefficient associated with the proposed training course;

performing processing of notifying the proposed training course; and performing processing of updating the database to change the weighting coefficient associated with the proposed training course after the proposed training course is taken.

15. The method according to claim 14, further comprising:

image processing the plurality of endoscopic images to perform scene discrimination at each of the plurality of predetermined steps of the endoscopic operation;

calculating, as a third evaluation parameter, a time required to perform each of the plurality of predetermined steps of the endoscopic operation based on the scene discrimination at each of the plurality of predetermined steps;

evaluating a value of a third skill of a doctor who performed the endoscopic operation based on the third evaluation parameter;

determining a proposed training course selected from a plurality of training courses relating to the third skill and stored in the database, wherein each of the plurality of training courses relating to the third skill is stored in association with a corresponding one of a third plurality of weighting coefficients, and wherein the proposed training course is selected based on the value of the third skill and the weighting coefficient associated with the proposed training course;

performing processing of notifying the proposed training course; and performing processing of updating the database to change the weighting coefficient associated with the proposed training course after the proposed training course is taken.

16. The method according to claim 15, further comprising:

receiving operation data of the endoscopic operation;

calculating, as a fourth evaluation parameter, at least one of air supply suction time and air supply suction amount at each step of the plurality of predetermined steps of the endoscopic operation based on the operation data of the endoscopic operation;
evaluating a value of a fourth skill of the doctor who performed the endoscopic operation based on the fourth evaluation parameter;
determining a proposed training course selected from a plurality of training courses relating to the fourth skill and stored in the database, wherein each of the plurality of training courses relating to the fourth skill is stored in association with a corresponding one of a fourth plurality of weighting coefficients, and wherein the proposed training course is selected based on the value of the fourth skill and the weighting coefficient associated with the proposed training course;
performing processing of notifying the proposed training course; and
performing processing of updating the database to change the weighting coefficient associated with the proposed training course after the proposed training course is taken.

17. A non-transitory computer-readable storage medium storing a program that, when executed, causes a computer to at least perform:
acquiring a plurality of endoscopic images acquired during an endoscopic operation;
perform at least one of matching processing between adjacent frames of the plurality of endoscopic images to extract an amplitude and frequency of vibrations from an optical flow of each of the plurality of endoscopic images;
calculating, as a first evaluation parameter, blurring amounts of the plurality of endoscopic images at each step of a plurality of predetermined steps of the endoscopic operation based on the amplitude and frequency of vibrations;
evaluating a value of a first skill of a doctor who performed the endoscopic operation based on the first evaluation parameter;
determining a proposed training course selected from a plurality of training courses relating to the first skill and stored in a database, wherein each of the plurality of training courses relating to the first skill is stored in association with a corresponding one of a plurality of weighting coefficient, and wherein the proposed training course is selected based on the value of the first skill and the weighting coefficient associated with the proposed training course;
performing processing of notifying the proposed training course; and
performing processing of updating the database to change the weighting coefficient associated with the proposed training course after the proposed training course is taken.

18. The non-transitory computer-readable storage medium according to claim 17, wherein the program, when executed, further causes the computer to perform:
acquiring a plurality of endoscopic images acquired during another endoscopic operation performed after the proposed training course is taken;
performing the at least one of matching processing between adjacent frames of the plurality of endoscopic images acquired during the another endoscopic operation to extract an amplitude and frequency of vibrations from an optical flow of each of the plurality of endoscopic images;
calculating, as an updated first evaluation parameter, blurring amounts of the plurality of endoscopic images at each step of a plurality of predetermined steps of the another endoscopic operation based on the amplitude and frequency of vibrations;
evaluating an updated value of the first skill of the doctor who performed the endoscopic operation based on the updated first evaluation parameter;
determining whether the updated value of the first skill is greater than the first value of the first skill; and
in response to determining that the updated value of the first skill is greater than the first value of the first skill, in performing the processing of updating the database, increasing the weighting coefficient associated with the proposed training course to increase the likelihood that the proposed training course will be selected in the future.

19. The non-transitory computer-readable storage medium according to claim 17, wherein the program, when executed, further causes the computer to perform:
performing image processing to extract regions of aggregated red pixels in the plurality of endoscopic images;
calculating, as a second evaluation parameter, a bleeding amount in each step of the plurality of predetermined steps of the endoscopic operation based on the regions of aggregated red pixels extracted;
evaluating a value of a second skill of the doctor who performed the endoscopic operation based on the second evaluation parameter;
determining a proposed training course selected from a plurality of training courses relating to the second skill and stored in the database, wherein each of the plurality of training courses relating to the second skill is stored in association with a corresponding one of a second plurality of weighting coefficients, and wherein the proposed training course is selected based on the value of the second skill and the weighting coefficient associated with the proposed training course;
performing processing of notifying the proposed training course; and
performing processing of updating the database to change the weighting coefficient associated with the proposed training course after the proposed training course is taken.

20. The non-transitory computer-readable storage medium according to claim 19, wherein the program, when executed, further causes the computer to perform:
image processing the plurality of endoscopic images to perform scene discrimination at each of the plurality of predetermined steps of the endoscopic operation;
calculating, as a third evaluation parameter, a time required to perform each of the plurality of predetermined steps of the endoscopic operation based on the scene discrimination at each of the plurality of predetermined steps;
evaluating a value of a third skill of a doctor who performed the endoscopic operation based on the third evaluation parameter;
determining a proposed training course selected from a plurality of training courses relating to the third skill and stored in the database, wherein each of the plurality of training courses relating to the third skill is stored in association with a corresponding one of a third plurality of weighting coefficients, and wherein the proposed training course is selected based on the value of the third skill and the weighting coefficient associated with the proposed training course;
performing processing of notifying the proposed training course; and performing processing of updating the database to change the weighting coefficient associated with the proposed training course after the proposed training course is taken.

\* \* \* \* \*